US011006628B2

(12) United States Patent
Fevre et al.

(10) Patent No.: US 11,006,628 B2
(45) Date of Patent: *May 18, 2021

(54) ANTIMICROBIAL POLYMERS CAPABLE OF SUPRAMOLECULAR ASSEMBLY

(71) Applicants: International Business Machines Corporation, Armonk, NY (US); AGENCY FOR SCIENCE, TECHNOLOGY AND RESEARCH, Connexis (SG)

(72) Inventors: Mareva B. Fevre, San Jose, CA (US); James L. Hedrick, Pleasanton, CA (US); Nathaniel H. Park, San Jose, CA (US); Victoria A. Piunova, Los Gatos, CA (US); Pang Kern Jeremy Tan, Singapore (SG); Yi Yan Yang, Singapore (SG)

(73) Assignees: INTERNATIONAL BUSINESS MACHINES CORPORATION, Armonk, NY (US); AGENCY FOR SCIENCE, TECHNOLOGY AND RESEARCH, Connexis (SG)

( * ) Notice: Subject to any disclaimer, the term of this patent is extended or adjusted under 35 U.S.C. 154(b) by 0 days.

This patent is subject to a terminal disclaimer.

(21) Appl. No.: 16/744,868

(22) Filed: Jan. 16, 2020

(65) Prior Publication Data

US 2020/0221692 A1 Jul. 16, 2020

Related U.S. Application Data

(62) Division of application No. 15/839,402, filed on Dec. 12, 2017, now Pat. No. 10,595,527.

(51) Int. Cl.
| | | |
|---|---|---|
| *A01N 25/10* | (2006.01) | |
| *A01N 37/26* | (2006.01) | |
| *A01N 43/50* | (2006.01) | |
| *A01N 47/44* | (2006.01) | |
| *C07C 279/10* | (2006.01) | |
| *C08L 79/02* | (2006.01) | |
| *C08G 69/26* | (2006.01) | |
| *C08G 73/02* | (2006.01) | |
| *C08L 101/00* | (2006.01) | |
| *A61Q 17/00* | (2006.01) | |

(52) U.S. Cl.
CPC ............ *A01N 25/10* (2013.01); *A01N 37/26* (2013.01); *A01N 43/50* (2013.01); *A01N 47/44* (2013.01); *C07C 279/10* (2013.01); *C08G 69/26* (2013.01); *C08G 73/0273* (2013.01); *C08L 79/02* (2013.01); *C08L 101/00* (2013.01); *A01N 2300/00* (2013.01); *A61Q 17/005* (2013.01)

(58) Field of Classification Search
CPC ........ A01N 25/10; A01N 37/26; A01N 43/50; A01N 47/44; C07C 279/10; C08G 69/26; C08G 73/0273; C08L 79/02; C08L 101/00; A61Q 17/005

See application file for complete search history.

(56) References Cited

U.S. PATENT DOCUMENTS

| | | |
|---|---|---|
| 3,632,623 A | 1/1972 | Becke et al. |
| 4,013,507 A | 3/1977 | Rembaum |
| 4,032,596 A | 6/1977 | Uffner et al. |
| 4,094,827 A | 6/1978 | McEntire |
| 4,166,894 A | 9/1979 | Schaper |
| 4,247,476 A | 1/1981 | Haase et al. |
| 4,348,536 A | 9/1982 | Blahak et al. |
| 4,698,391 A | 10/1987 | Yacobucci et al. |
| 4,794,031 A | 12/1988 | Leir et al. |
| 4,883,655 A | 11/1989 | Login et al. |
| 5,419,897 A | 5/1995 | Drake et al. |
| 5,681,862 A | 10/1997 | Hollis et al. |
| 6,767,549 B2 | 7/2004 | Mandeville, III et al. |
| 6,955,806 B2 | 10/2005 | Fitzpatrick et al. |
| 8,541,477 B2 | 9/2013 | Alabdulrahman et al. |
| 10,836,864 B2 | 11/2020 | Fevre et al. |
| 2006/0002889 A1 | 1/2006 | Fitzpatrick |
| 2007/0025954 A1 | 2/2007 | Fitzpatrick et al. |
| 2007/0106061 A1 | 5/2007 | Zollinger et al. |
| 2012/0202979 A1 | 8/2012 | Wu |
| 2013/0281515 A1 | 10/2013 | Coady et al. |
| 2014/0275469 A1 | 9/2014 | Dhal et al. |
| 2015/0038392 A1 | 2/2015 | Scheuing et al. |
| 2016/0374335 A1 | 12/2016 | Chan et al. |
| 2016/0375150 A1 | 12/2016 | Wu |

FOREIGN PATENT DOCUMENTS

| | | |
|---|---|---|
| CN | 1192649 A | 9/1998 |
| CN | 1254334 A | 5/2000 |
| CN | 1518621 A | 8/2004 |

(Continued)

OTHER PUBLICATIONS

Non-Final Office Action received for U.S. Appl. No. 15/839,410 dated Apr. 22, 2020, 38 pages.

(Continued)

*Primary Examiner* — Alma Pipic

(74) *Attorney, Agent, or Firm* — Amin, Turocy & Watson, LLP

(57) ABSTRACT

Techniques regarding chemical compounds with antimicrobial functionality are provided. For example, one or more embodiments describe herein can comprise a monomer that can comprise a molecular backbone. The molecular backbone can comprise a bis(urea)guanidinium structure covalently bonded to a functional group, which can comprise a radical. Also, the monomer can have supramolecular assembly functionality.

10 Claims, 17 Drawing Sheets

(56) References Cited

FOREIGN PATENT DOCUMENTS

| | | |
|---|---|---|
| CN | 101426507 A | 5/2009 |
| CN | 101646728 A | 2/2010 |
| CN | 105482105 A | 4/2016 |
| DE | 2824743 A1 | 12/1978 |
| GB | 2000164 A | 1/1979 |
| JP | H03255139 A | 11/1991 |
| JP | 2004-224734 A | 8/2004 |
| JP | 2008-214529 A | 9/2008 |
| WO | 9702744 A1 | 1/1997 |
| WO | 9854140 A1 | 12/1998 |
| WO | 02080939 A2 | 10/2002 |
| WO | 02099192 A2 | 12/2002 |
| WO | 2016/178634 A1 | 11/2016 |
| WO | 2016/186581 A1 | 11/2016 |
| WO | 2016/209732 A1 | 12/2016 |

OTHER PUBLICATIONS

Liu, et al., "Highly potent antimicrobial polyionenes with rapid killing kinetics, skin biocompatibility and in vivo bactericidal activity", Biomaterials, 2017, vol. 127, pp. 36-48.

Williams, et al., "Recent advances in the synthesis and structure—property relationships of ammonium ionenes", Progress in Polymer Science, 2009, vol. 34., pp. 762-782.

Narita, et al., "Effects of charge density and hydrophobicity of ionene polymer on cell binding and viability", Colloid Polym. Sci, 2000, pp. 884-887.

Mattheis, et al., "Closing One of the Last Gaps in Polyionene Compositions: Alkyloxyethylammonium Ionenes as Fast-Acting Biocides", Macromolecular Bioscience, 2012, vol. 12., pp. 341-349.

Strassburg, et al., "Nontoxic, Hydrophilic Cationic Polymers—Identified as Class of Antimicrobial Polymers", Macromolecular Bioscience, 2015, vol. 15., pp. 1710-1723.

Mayr, et al., "Antimicrobial and Hemolytic Studies of a Series of Polycations Bearing Quaternary Ammonium Moieties: Structural and Topological Effects", International Journal of Molecular Sciences, 2017, vol. 18, No. 303., 8 pages.

Tamami, Synthesis and Characterization of Ammonium Ionenes Containing Hydrogen Bonding Functionalities, Virginia Polytechnic Institute and State University, Dec. 6, 2012,108 pages.

Brown et al., "The Structure Activity Relationship of Urea Derivatives as Anti-Tuberculosis Agents", Bioorg Med Chem, Sep. 15, 2011, vol. 19, No. 18, pp. 5585-5595.

Williams, "Influence of Electrostatic Interactions and Hydrogen Bonding on the Thermal and Mechanical Properties of Step-Growth Polymers", Virginia Polytechnic Institute and State University, Oct. 21, 2008, 375 pages.

International Search Report and Written Opinion received for PCT Application Serial No. PCT/IB2018/059622, dated Mar. 28, 2019, 9 pages.

International Search Report and Written Opinion received for PCT Application Serial No. PCT/IB2018/059626, dated Apr. 15, 2019, 8 pages.

International Search Report and Written Opinion received for PCT Application Serial No. PCT/IB2018/059620, dated Mar. 27, 2019, 11 pages.

International Search Report and Written Opinion received for PCT Application Serial No. PCT/IB2018/059624 dated Apr. 17, 2019, 8 pages.

Non-Final Office Action received for U.S. Appl. No. 15/839,388 dated Jul. 10, 2019, 52 pages.

Murakami et al., "Syntheses of Macrocyclic Enzyme Models, Part 4. Preparation and Characterization of Cationic Octopus Azaparacyclophanes", Organic and Bio-Organic Chemistry, Journal of the Chemical Society, Perkin Transactions 1, Issue 11, Jan. 1, 1981, pp. 2800-2808.

Non-Final Office Action received for U.S. Appl. No. 15/839,199 dated Jun. 26, 2019, 66 pages.

Tiecco et al., "Biocidal and inhibitory activity screening of de novo synthesized surfactants against two eukaryotic and two prokaryotic microbial species", Science Direct, Colloids and Surfaces B: Biointerfaces, vol. 111, Nov. 1, 2013, 35 pages.

Non-Final Office Action received for U.S. Appl. No. 15/839,402 dated Jun. 26, 2019, 56 pages.

Odagi et al., "Origin of Stereocontrol in Guanidine-Bisurea Bifunctional Organocatalyst That Promotes α-Hydroxylation of Tetralone-Derived β-Ketoesters: Asymmetric Synthesis of β- and γ-Substituted Tetralone Derivatives via Organocatalytic Oxidative Kinetic Resolution", Journal of the American Chemical Society, Jan. 2015, pp. 1909-1915.

Magri et al., "Rethinking the old antiviral drug moroxydine: Discovery of novel analogues as anti-hepatitis C virus (HCV) agents", Bioorganic and Medicinal Chemistry Letters, vol. 25, No. 22, Nov. 2015, pp. 5372-5376.

Non-Final Office Action received for U.S. Appl. No. 15/839,415 dated Jul. 10, 2019, 29 pages.

International Search Report and Written Opinion received for PCT Application Serial No. PCT/IB2018/059621 dated Apr. 10, 2019, 8 pages.

Final Office Action received for U.S. Appl. No. 15/839,199 dated Sep. 26, 2019, 25 pages.

Non-Final Office Action received for U.S. Appl. No. 15/839,270 dated Sep. 16, 2019, 70 pages.

Non-Final Office Action received for U.S. Appl. No. 15/839,397 dated Sep. 17, 2019, 47 pages.

Wettig et al., "Thermodynamic and aggregation properties of aza- and imino-substituted gemini surfactants designed for gene delivery", Physical Chemistry Chemical Physics, vol. 9, 2007, pp. 871-877.

Notice of Allowance received for U.S. Appl. No. 15/839,402 dated Oct. 24, 2019, 113 pages.

Chahboune et al., "Application of liquid chromatography/electrospray ionization tandem mass spectrometry for the elucidation of hydroxyl radical oxidation of metsulfuron methyl and related sulfonylurea pesticide products: evidence for the triazine skeleton scission", Rapid Communications in Mass Spectrometry, vol. 29, Sep. 2015, pp. 1370-1380.

Rafqah et al., "Kinetics and mechanism of the degradation of the pesticde metsulfuron methyl induced by excitation of iron(III) aqua complexes in aqueous solutions: steady state and transient absorption spectroscopy studies", Photochem. Photobial. Sci., vol. 3, 2004, pp. 296-304.

Si et al., "Leaching and degradation of ethametsulfuron-methyl in soil", Cehmosphere, vol. 60, 2005, pp. 601-609.

Li-Feng et al., "Biodegradation of Ethametsulfuron-Methyl by *Pseudomonas* sp. SW4 Isolated from Contaminated Soil", Curr Microbial, vol. 55, 2007, pp. 420-426.

Non-Final Office Action received for U.S. Appl. No. 15/839,410 dated Oct. 31, 2019, 41 pages.

Final Office Action received for U.S. Appl. No. 15/839,415 dated Nov. 6, 2019, 29 pages.

Advisory Action received for U.S. Appl. No. 15/839,199, dated Nov. 19, 2019, 16 pages.

Final Office Action received for U.S. Appl. No. 15/839,388 dated Dec. 5, 2019, 43 pages.

Non-Final Office Action received for U.S. Appl. No. 15/839,199 dated Dec. 26, 2019, 156 pages.

Haque et al., Synthesis, Characterization, and Crystal Structures of Bis-Imidazolium Salts and Respective Dinuclear Ag(I) N-Heterocyclic Carbene Complexes: In Vitro Anticancer Studies against "Human Colon Cancer" and "Breast Cancer", Hindawi Publishing Corporation Journal of Chemistry, 2013, 11 pages.

Wynne et al., "Synthesis and Development of a Multifunctional Self-Decontaminating Polyurethane Coating", Applied Materials and Interfaces, 2011, pp. 2005-2011.

Ol'Khovik et al., "Synthesis, Antimicrobial and Antifungal Activity of Double Quaternary Alnmonium Salts of Biphenyls", Russian Journal of General Chemistry, vol. 83, No. 2, 2013, pp. 329-335.

(56) References Cited

OTHER PUBLICATIONS

Jones et al., ortlo Substitution Rearrangement vs. β)-Elimination of Quaternary Ammonium Ion-Alcohols and Methyl Ether with Excess Sodium Amide[1], vol. 27 ,1962, pp. 806-814.

Menger et al., "Synthesis and Properties of Nine New Polyhydroxylated Surfactants", Langmuir, vol. 12, No. 6, 1996, pp. 1471-1473.

Final Office Action received for U.S. Appl. No. 15/839,397 dated Dec. 16, 2019, 31 pages.

Shen et al., "Synthesis of Highly Ordered Thermally Stable Cubic Mesostructured Zirconium Oxophosphate Templated by Tri-Headgroup Quaternary Ammonium Surfactants", Chem. Mater, vol. 15, No. 21, 2003, pp. 4046-4051.

Wang et al., "Transfection and structural properties of phytanyl substituted gemini surfactant-based vectors for gene delivery", Phys. Chem. Chem. Phys., 2013, vol. 15, pp. 20510-20516.

Non-Final Office Action received for U.S. Appl. No. 16/829,370 dated Sep. 8, 2020, 50 pages.

Final Office Action received for U.S. Appl. No. 16/829,370 dated Dec. 31, 2020, 32 pages.

German Office Action for German Application No. 11 2018 005 633.3 dated Jan. 1, 2021, 3 pages.

DISSOLVING AN AMINE MONOMER WITH AN ELECTROPHILE IN A SOLVENT, THE AMINE MONOMER COMPRISING A MOLECULAR BACKBONE, AND THE MOLECULAR BACKBONE COMPRISING A BIS(UREA)GUANIDINIUM STRUCTURE AND AN ESTER FUNCTIONAL GROUP — 1202

POLYMERIZING THE AMINE MONOMER AND THE ELECTROPHILE TO FORM AN IONENE UNIT, THE IONENE UNIT COMPRISING THE ESTER FUNCTIONAL GROUP AND A CATION LOCATED ALONG THE MOLECULAR BACKBONE, WHEREIN THE IONENE UNIT HAS ANTIMICROBIAL FUNCTIONALITY — 1204

1400

| Ionene Composition | SA (μg/mL) | EC (μg/mL) | PA (μg/mL) | CA (μg/mL) | Hemolysis (HC50) |
|---|---|---|---|---|---|
| First Ionene Composition 702 | 31 | 31 | 63 | 2 | >2000 |
| Second Ionene Composition 706 | 4 | 16 | 16 | 16 | >2000 |
| Third Ionene Composition 1002 | 16 | 16 | 8 | 4 | >2000 |
| Fourth Ionene Composition 1008 | 8 | 8 | 8 | 4 | >2000 |
| Fifth Ionene Composition 1302 | 63 | 31 | >500 | 31 | >2000 |

| CONTACTING A PATHOGEN WITH A CHEMICAL COMPOUND, THE CHEMICAL COMPOUND COMPRISING AN IONENE UNIT, THE IONENE UNIT COMPRISING A MOLECULAR BACKBONE AND A CATION DISTRIBUTED ALONG THE MOLECULAR BACKBONE, AND THE MOLECULAR BACKBONE COMPRISING A BIS(UREA)GUANIDINIUM STRUCTURE, WHEREIN THE IONENE UNIT HAS ANTIMICROBIAL FUNCTIONALITY | 1702 |

| ELECTROSTATICALLY DISRUPTING A MEMBRANE OF THE PATHOGEN UPON CONTACTING THE PATHOGEN WITH THE CHEMICAL COMPOUND | 1704 |

ANTIMICROBIAL POLYMERS CAPABLE OF SUPRAMOLECULAR ASSEMBLY

BACKGROUND

The subject disclosure relates to one or more ionenes and/or polyionenes with antimicrobial functionalities, and more specifically, to one or more ionene and/or polyionene compositions capable of supramolecular assembly.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, methods and/or compositions regarding ionenes and/or polyionenes with antimicrobial functionality are described.

According to an embodiment, a monomer is provided. The monomer can comprise a molecular backbone comprising a bis(urea)guanidinium structure covalently bonded to a functional group, which can comprise a radical. The monomer can have supramolecular assembly functionality.

According to an embodiment, a chemical compound is provided. The chemical compound can comprise an ionene unit comprising a cation distributed along a degradable backbone. The degradable backbone can comprise a bis(urea)guanidinium structure. Also, the ionene unit has antimicrobial functionality.

According to an embodiment, a method is provided. The method can comprise aminolyzing an ester group of a monomer with an aminolysis reagent. The monomer can comprise the ester group covalently bonded to a guanidinium group. Also, the aminolyzing can form a molecular backbone that can comprise a bis(urea)guanidinium structure.

According to an embodiment, a method is provided. The method can comprise dissolving an amine monomer with an electrophile in a solvent. The amine monomer can comprise a molecular backbone. The molecular backbone can comprise a bis(urea)guanidinium structure. The method can also comprise polymerizing the amine monomer and the electrophile to form an ionene unit. Further, the ionene unit can comprise a cation located along the molecular backbone. Also, the ionene unit can have antimicrobial functionality.

According to an embodiment, a method is provided. The method can comprise dissolving a first amine monomer, a second amine monomer, and an electrophile in solvent. The first amine monomer can comprise a molecular backbone, which can comprise a bis(urea)guanidinium structure. The second amine monomer can comprise a degradable backbone, which can comprise a terephthalamide structure. The method can further comprise polymerizing the first amine monomer and the second amine monomer with the electrophile to form a copolymer. The copolymer can comprise a first cation distributed along the molecular backbone and a second cation distributed along the degradable backbone. Also, the copolymer can have antimicrobial functionality.

BRIEF DESCRIPTION OF THE DRAWINGS

FIG. 12 illustrates a flow diagram of an example, non-limiting method that can facilitate generating one or more ionene units in accordance with one or more embodiments described herein.

FIG. 14 illustrates a diagram of an example, non-limiting chart that can depict antimicrobial functionality of various ionene compositions in accordance with one or more of the embodiments described herein.

FIG. 17 illustrates a diagram of an example, non-limiting method that can facilitate killing of a pathogen with an ionene in accordance with one or more embodiments described herein.

DETAILED DESCRIPTION

Figure 1A:
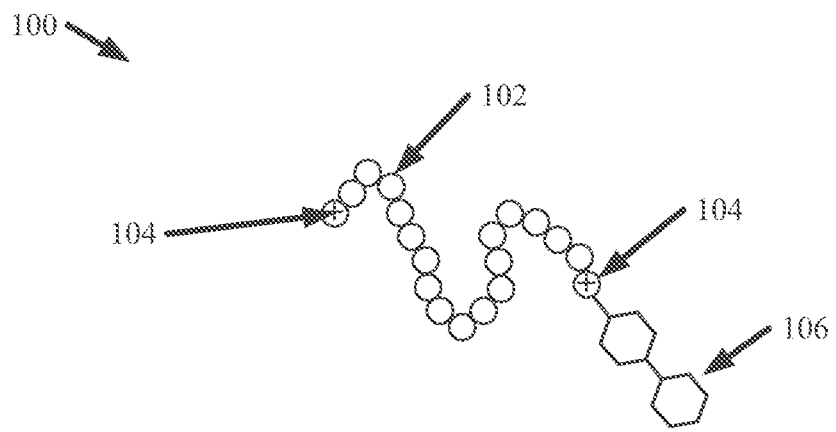
FIG. 1A illustrates a diagram of an example, non-limiting ionene unit in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

The discovery and refinement of antibiotics was one of the crowning achievements in the 20$^{th}$ century that revolutionized healthcare treatment. For example, antibiotics such as penicillin, ciprofloxacin and, doxycycline can achieve microbial selectivity through targeting and disruption of a specific prokaryotic metabolism, while concurrently, remaining benign toward eukaryotic cells to afford high selectivity. If properly dosed, they could eradicate infection. Unfortunately, this therapeutic specificity of antibiotics also leads to their undoing as under-dosing (incomplete kill) allows for minor mutative changes that mitigate the effect of the antibiotic leading to resistance development. Consequently, nosocomial infections, caused by medication-resistant microbes such as methicillin-resistant *Staphylococcus aureus* (MRSA), multi-medication-resistant *Pseudomonas aeruginosa* and vancomycin-resistant Enterococci (VRE) have become more prevalent. An added complexity is the pervasive use of antimicrobial agents in self-care products, sanitizers and hospital cleaners etc, including anilide, bis-phenols, biguanides and quaternary ammonium compounds, where a major concern is the development of cross- and co-resistance with clinically used antibiotics, especially in a hospital setting. Another unfortunate feature with triclosan, for example, is its cumulative and persistent effects in the skin. Moreover, biofilms have been associated with numerous nosocomial infections and implant failure, yet the eradication of biofilms is an unmet challenge to this date. Since antibiotics are not able to penetrate through extracellular polymeric substance that encapsulates bacteria in the biofilm, further complexities exist that lead to the development of medication resistance.

However, polymers having a cationic charge can provide electrostatic disruption of the bacterial membrane interaction. Furthermore, cationic polymers are readily made amphiphilic with addition of hydrophobic regions permitting both membrane association and integration/lysis. The amphiphilic balance has shown to play an important effect not only in the antimicrobial properties but also in the hemolytic activity. Many of these antimicrobial polymers show relatively low selectivity as defined by the relative toxicity to mammalian cells or hemolysis relative to pathogens.

Additionally, chemical compound (e.g., monomers and/or polymers) that can supramolecularly assemble with biological entities can demonstrate a high efficacy regarding the eradication of infections. In particular, chemical compounds with numerous hydrogen bond donors and/or acceptors are capable of assembling on the surface of a microbe.

Therefore, various embodiments described herein can regard chemical compounds (e.g., monomers and/or polymers) that can comprise one or more ionenes with antimicrobial functionality. Additionally, one or more of the ionenes described herein can have antimicrobial functionality and/or supramolecular assembly functionality. For example, one or more of the ionenes described herein can comprise one or more bis(urea) guanidinium structures.

As used herein, the term "ionene" can refer to a polymer unit, a copolymer unit, and/or a monomer unit that can comprise a nitrogen cation and/or a phosphorus cation distributed along, and/or located within, a molecular backbone, thereby providing a positive charge. Example nitrogen cations include, but are not limited to: quaternary ammonium cations, protonated secondary amine cations, protonated tertiary amine cations, and/or imidazolium cations. Example, phosphorus cations include, but are not limited to: quaternary phosphonium cations, protonated secondary phosphine cations, and protonated tertiary phosphine cations. As used herein, the term "molecular backbone" can refer to a central chain of covalently bonded atoms that form the primary structure of a molecule. In various embodiments described herein, side chains can be formed by bonding one or more functional groups to a molecular backbone. As used herein, the term "polyionene" can refer to a polymer that can comprise a plurality of ionenes. For example, a polyionene can comprise a repeating ionene.

FIG. 1A illustrates a diagram of an example, non-limiting ionene unit 100 in accordance with one or more embodiments described herein. The ionene unit 100 can comprise a molecular backbone 102, one or more cations 104, and/or one or more hydrophobic functional groups 106. In various embodiments, an ionene and/or a polyionene described herein can comprise the ionene unit 100. For example, a polyionene described herein can comprise a plurality of ionenes bonded together, wherein the bonded ionenes can have a composition exemplified by ionene unit 100.

Figure 1B:
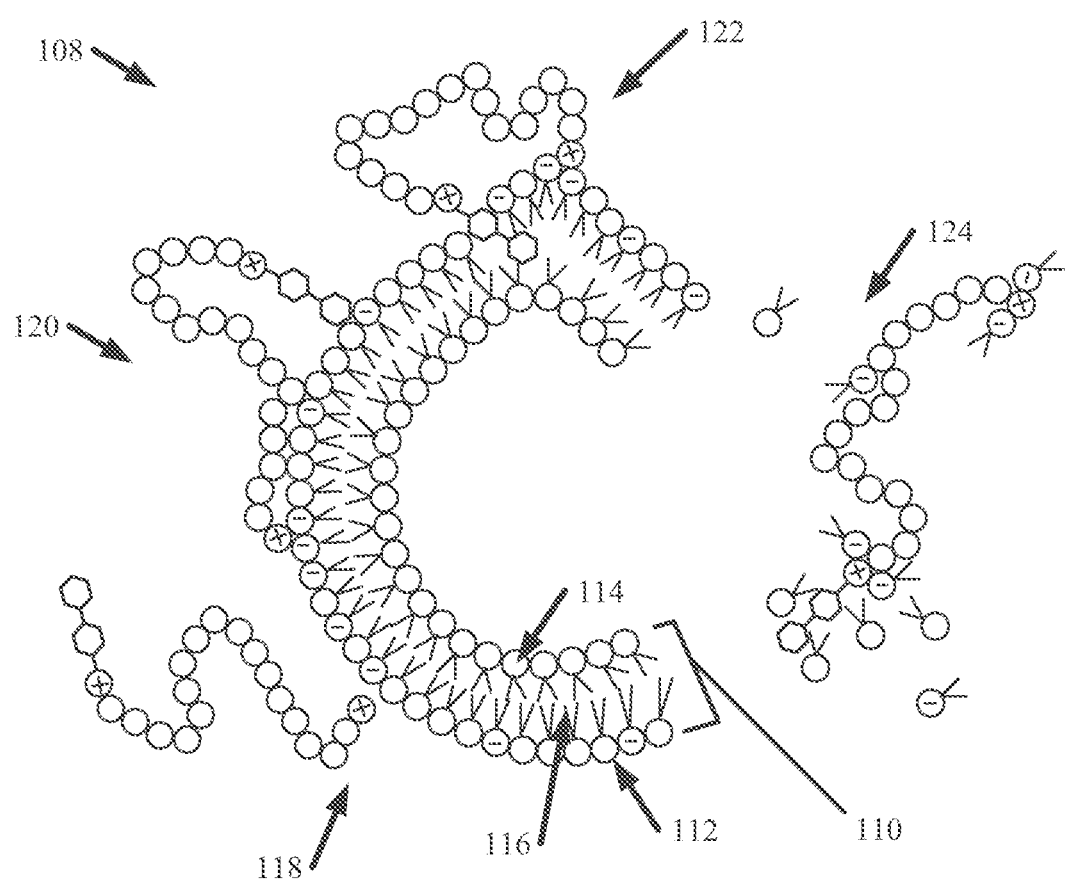
FIG. 1B illustrates a diagram of an example, non-limiting lysis process that can be performed by one or more ionene units in accordance with one or more embodiments described herein.

The molecular backbone 102 can comprise a plurality of covalently bonded atoms (illustrated as circles in FIGS. 1A and 1B). The atoms can be bonded in any desirable formation, including, but not limited to: chain formations, ring formations, and/or a combination thereof. The molecular backbone 102 can comprise one or more chemical structures including, but not limited to: alkyl structures, aryl structures, alkane structures, aldehyde structures, ester structures, carboxyl structures, carbonyl structures, amine structures, amide structures, phosphide structures, phosphine structures, a combination thereof, and/or the like. One of ordinary skill in the art will recognize that the number of atoms that can comprise the molecular backbone can vary depending of the desired function of the ionene unit 100. For example, while nineteen atoms are illustrated in FIG. 1A, a molecular backbone 102 that can comprise dozens, hundreds, and/or thousands of atoms is also envisaged.

Located within the molecular backbone 102 are one or more cations 104. As described above, the one or more cations 104 can comprise nitrogen cations and/or phosphorous cations. The cations 104 can be distributed along the molecular backbone 102, covalently bonded to other atoms within the molecular backbone 102. In various embodiments, the one or more cations 104 can comprise at least a portion of the molecular backbone 102. One of ordinary skill in the art will recognize that the number of a cations 104 that can comprise the ionene unit 100 can vary depending of the desired function of the ionene unit 100. For example, while two cations 104 are illustrated in FIG. 1A, an ionene unit 100 that can comprise dozens, hundreds, and/or thousands of cations 104 is also envisaged. Further, while FIG. 1A illustrates a plurality of cations 104 evenly spaced apart, other configurations wherein the cations 104 are not evenly spaced apart are also envisaged. Also, the one or more cations 104 can be located at respective ends of the molecular backbone 102 and/or at intermediate portions of the molecular backbone 102, between two or more ends of the molecular backbone 102. The one or more cations 104 can provide a positive charge to one or more locations of the ionene unit 100.

The one or more hydrophobic functional groups 106 can be bonded to the molecular backbone 102 to form a side chain. The one or more of the hydrophobic functional groups 106 can be attached to the molecular backbone 102 via bonding with a cation 104. Additionally, one or more hydrophobic functional groups 106 can be bonded to an electrically neutral atom of the molecular backbone 102. The ionene unit 100 can comprise one or more hydrophobic functional groups 106 bonded to: one or more ends of the molecular backbone 102, all ends of the molecular backbone 102, an intermediate portion (e.g., a portion between two ends) of the molecular backbone 102, and/or a combination thereof.

While a biphenyl group is illustrated in FIG. 1A as the hydrophobic functional group 106, other functional groups that are hydrophobic are also envisaged. Example, hydrophobic functional groups 106 can include, but are not limited to: alkyl structures, aryl structures, alkane structures, aldehyde structures, ester structures, carboxyl structures, carbonyl structures, carbonate structures, alcohol structures, a combination thereof, and/or the like. In various embodiments, the one or more hydrophobic functional groups 106 can comprise the same structure. In other embodiments, one or more of the hydrophobic functional groups 106 can comprise a first structure and one or more other hydrophobic functional groups 106 can comprise another structure.

FIG. 1B illustrates a diagram of an example, non-limiting lysis process 108 that can be facilitated by the ionene unit 100 in accordance with one or more embodiments described herein. Repetitive description of like elements employed in other embodiments described herein is omitted for sake of brevity. The lysis process 108 can comprise a plurality of stages, which can collectively comprise an attack mechanism that can be performed by the ionene unit 100 against a pathogen cell. Example pathogen cells can include, but are not limited to: Gram-positive bacteria cells, Gram-negative bacteria cells, fungi cells, and/or yeast cells.

The target pathogen cell can comprise a membrane having a phospholipid bilayer 110. In various embodiments, the membrane can be an extracellular matrix. The phospholipid bilayer 110 can comprise a plurality of membrane molecules 112 covalently bonded together, and the membrane molecules 112 can comprise a hydrophilic head 114 and one or more hydrophobic tails 116. Further, one or more of the plurality of membrane molecules 112 can be negatively charged (as illustrated in FIG. 1B with a "-" symbol).

At 118, electrostatic interaction can occur between the positively charged cations 104 of the ionene unit 100 and one or more negatively charged membrane molecules 112. For example, the negative charge of one or more membrane molecules 112 can attract the ionene unit 100 towards the membrane (e.g., the phospholipid bilayer 110). Also, the electrostatic interaction can electrostatically disrupt the integrity of the membrane (e.g., phospholipid bilayer 110). Once the ionene unit 100 has been attracted to the membrane (e.g., phospholipid bilayer 110), hydrophobic membrane integration can occur at 120. For example, at 120 one or more hydrophobic functional groups 106 of the ionene unit 100 can begin to integrate themselves into the phospholipid bilayer 110. While the positively charged portions of the ionene unit 100 are attracted, and electrostatically disrupting, one or more negatively charged membrane molecules 112 (e.g., one or more hydrophilic heads 114), the one or more hydrophobic functional groups 106 can insert themselves between the hydrophilic heads 114 to enter a hydrophobic region created by the plurality of hydrophobic tails 116.

As a result of the mechanisms occurring at 118 and/or 120, destabilization of the membrane (e.g., the phospholipid bilayer 110) can occur at 122. For example, the one or more hydrophobic functional groups 106 can serve to cleave one or more negatively charged membrane molecules 112 from adjacent membrane molecules 112, and the positively charged ionene unit 100 can move the cleaved membrane segment (e.g., that can comprise one or more negatively charged membrane molecules 112 and/or one or more neutral membrane molecules 112 constituting a layer of the phospholipid bilayer 110) away from adjacent segments of the membrane (e.g., adjacent segments of the phospholipid bilayer 110). As cleaved segments of the membrane (e.g., the phospholipid bilayer 110) are pulled away, they can fully detach from other membrane molecules 112 at 124, thereby forming gaps in the membrane (e.g., the phospholipid bilayer 110). The formed gaps can contribute to lysis of the subject pathogen cell. In various embodiments, a plurality of ionene units 100 can perform the lysis process 108 on a cell simultaneously. Furthermore, the ionene units 100 participating in a lysis process 108 need not perform the same stages of the attack mechanism at the same time.

Figure 2:
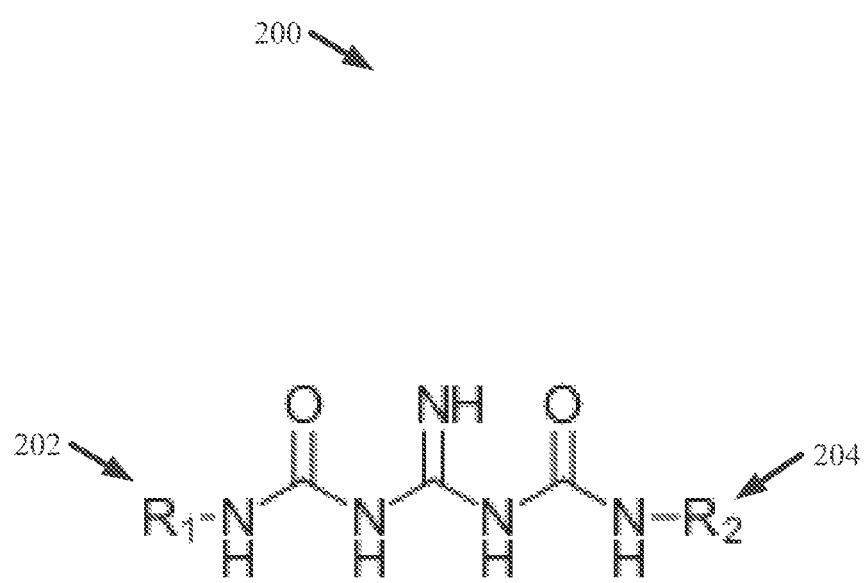
FIG. 2 illustrates a diagram of an example, non-limiting chemical formula that can characterize one or more amine monomers in accordance with one or more embodiments described herein.

FIG. 2 illustrates a diagram of an example, non-limiting chemical formula 200 that can characterize the structure of an amine monomer that can be polymerized to form a variety of ionene units 100 in accordance with one or more embodiments described herein. Repetitive description of like elements employed in other embodiments described herein is omitted for sake of brevity.

As shown in FIG. 2, one or more amine monomer characterized by chemical formula 200 can comprise a degradable molecular backbone 102. Further, the molecular backbone 102 can comprise one or more bis(urea)guanidinium structures. In various embodiments, the one or more amine monomers characterized by chemical formula 200 can be derived from 1,3-bis(butoxycarbonyl)guanidine, wherein the one or more guanidinium groups of the one or more bis(urea)guanidinium structures can be derived from the 1,3-bis(butoxycarbonyl)guanidine. However, one or more embodiments of chemical formula 200 can comprise one or more bis(urea)guanidium structures derived from one or more molecules other than 1,3-bis(butoxycarbonyl)guanidine.

The one or more amine monomers characterized by chemical formula 200 can also comprise one or more functional groups covalently boned to the one or more bis(urea)guanidium structures. For example, as shown in FIG. 2, "$R_1$" can represent a first functional group 202 covalently bonded to the one or more bis(urea)guanidium structures. One or more first functional group 202 can comprise one or more amino groups, one or more phosphine groups, and/or one or more ester groups. For example, the first functional group 202 can comprise one or more primary amino groups, one or more secondary amino groups, one or more tertiary amino groups, one or more imidazole groups, and/or one or more heterocycles (e.g., one or more pyridine groups). In another example, the first functional group 202 can comprise one or more primary phosphines, one or more secondary phosphines, and/or one or more tertiary phosphines. In another example, the first functional group 202 can comprise one or more ester groups, which can comprise one or more alkyl groups and/or one or more aryl groups. Thus, the first functional group 202 can comprise: one or more groups (e.g., amino groups and/or phosphine groups) that can subsequently become cationic groups (e.g., comprising one or more cations 104) during a polymerization of the one or more amine monomers characterized by chemical formula 200; and/or one or more groups (e.g., ester groups) that can contribute degradability to the molecular backbone 102 of the one or more amine monomers characterized by chemical formula 200.

As shown in FIG. 2, "$R_2$" can represent a second functional group 204 covalently bonded to the one or more bis(urea)guanidium structures. One or more second functional groups 204 can comprise one or more radicals, which can subsequently form one or more cations 104 in a polymerization of the one or more amine monomers characterized by chemical formula 200. The second functional group 204 can comprise one or more amino groups and/or one or more phosphine groups. For example, the second functional group 204 can comprise one or more primary amino groups, one or more secondary amino groups, one or more tertiary amino groups one or more imidazole groups, and/or one or more heterocycles (e.g., one or more pyridine groups). In another example, the second functional group 204 can comprise one or more primary phosphines, one or more secondary phosphines, and/or one or more tertiary phosphines. In one or more embodiments, the first functional group 202 and/or the second functional group 204 can comprise different structures. In various embodiments, the first functional group 202 and/or the second functional group 204 can comprise the same structure.

Figure 3:
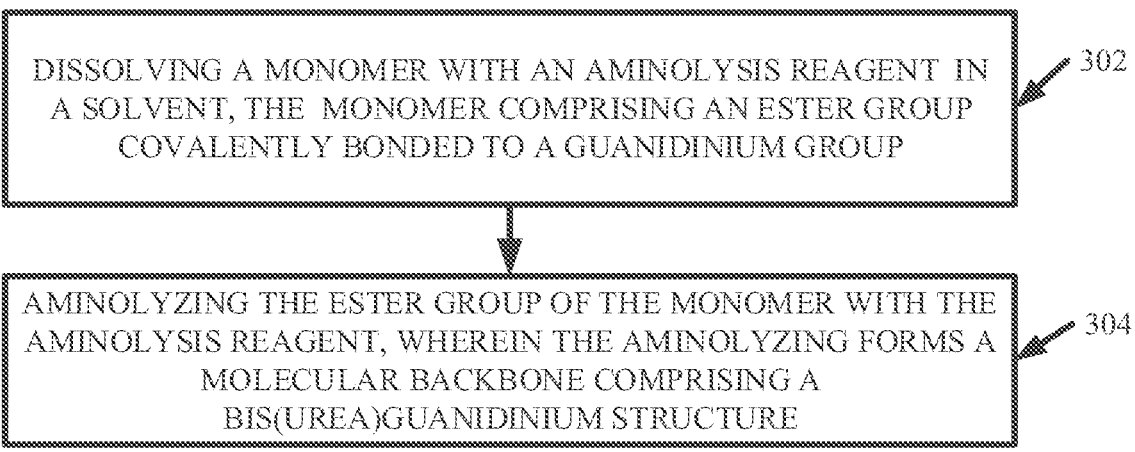
FIG. 3 illustrates a flow diagram of an example, non-limiting method that can facilitate generating one or more amine monomers in accordance with one or more embodiments described herein.

FIG. 3 illustrates a flow diagram of an example, non-limiting method 300 that can facilitate generating one or more amine monomers that can be characterized by chemical formula 200. Repetitive description of like elements employed in other embodiments described herein is omitted for sake of brevity.

At 302, the method 300 can comprise dissolving one or more monomers with one or more aminolysis reagents in a solvent. The one or more monomers can comprise a molecular backbone 102, which can comprise one or more ester groups covalently bonded to one or more guanidinium groups. Additionally, the one or more monomers can further comprise a structure selected from a group that can include, but is not limited to: alkyl amine groups, hetero cyclic amine groups, a combination thereof, and/or the like. Moreover, the one or more monomers can be degradable (e.g., biodegradable). In one or more embodiments, the one or more monomers can comprise 1,3-bis(butoxycarbonyl)guanidine.

The one or more aminolysis reagents can comprise one or more molecules that can facilitate an aminolysis process. For example, the one or more aminolysis reagents can be diamines. A first amino group of the diamines can include, but is not limited to, a primary amino group and/or a secondary amino group. Also, a second amino group of the diamines can include, but is not limited to: a primary amino group, a secondary amino group, a tertiary amino group, and/or an imidazole group. For example, in one or more embodiments the secondary amino group can be a tertiary amino group and/or an imidazole group.

The solvent can be an organic solvent. Additionally, the solvent can be an aprotic solvent, a dipolar solvent, and/or an alcohol. Example solvents can include but are not limited to: dimethyl formamide ("DMF"), methanol, tetrahydrofuran ("THF"), a combination thereof, and/or the like. To facilitate the dissolving, the method 300 can further comprise stirring one or more amine monomers, the one or more aminolysis reagents, and the solvent at a temperature greater than or equal to 15 degrees Celsius (° C.) and less than or equal to 150° C. for a period of time greater than or equal to 8 hours and less than or equal to 72 hours (e.g., greater than or equal to 12 hours and less than or equal to 24 hours). Additionally, an organocatylst (e.g., triazabicyclodecene ("TBD")) can be dissolved at 302.

At 304, the method 300 can comprise aminolyzing one or more ester groups of the one or more monomers with the aminolysis reagent (e.g., a diamine) to form one or more amine monomers that can be characterized by chemical formula 200. For example, the one or more first amino groups of one or more diamine aminolysis reagents can donate a hydrogen to facilitate covalent bonding of the aminolysis agent with one or more ester groups of the one or more amino monomers. As a result of bonding the one or more first amino groups of one or more diamine aminolysis reagents to one or more ester groups of the one or more monomers, one or more second amino groups of the one or more diamines can form the first functional group 202 and/or the second functional group 204 (e.g., generation of one or more urea linkages).

For example, an amine monomer formed at 304 (e.g., characterized by chemical formula 200) can comprise a molecular backbone 102 with one or more bis(urea)guanidinium structures. For example, the one or more urea groups of the one or more bis(urea) guanidinium structures can be formed at 304 by replacing an oxygen of one or more ester groups of the monomer reactant with a nitrogen of one or more first amino groups of the aminolysis reagent. Further, one or more functional groups (e.g., first functional group 202 and/or second functional group 204) can be bonded to the one or more bis(urea)guanidinium structures and can comprise one or more second amino groups of the aminolysis reagent. For instance, one or more second amino groups of the aminolysis reagent can comprise one or more tertiary amino groups and/or one or more imidazole groups; thus, said one or more second amino groups can comprise one or more functional groups (e.g., first functional group 202 and/or second functional group 204) covalently bonded to one or more bis(urea)guanidinium structures at 304.

Figure 4A:
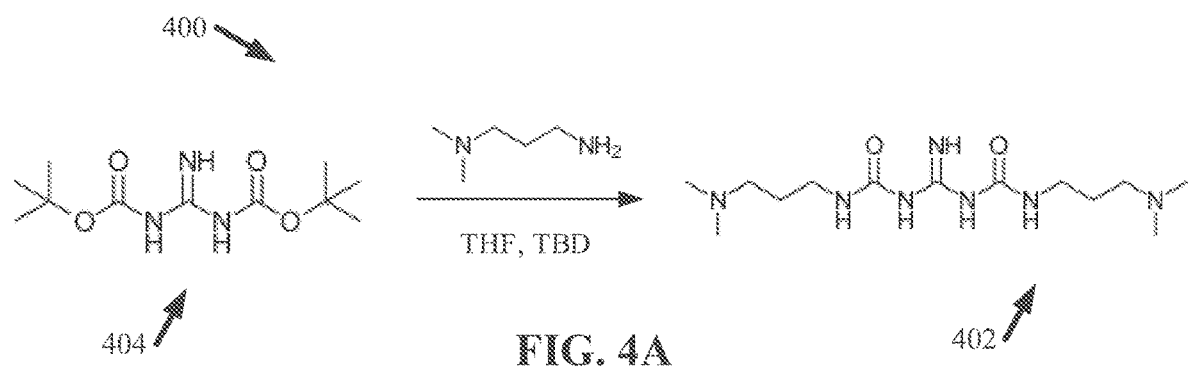
FIG. 4A illustrates a diagram of an example, non-limiting scheme that can facilitate generating one or more amine monomers in accordance with one or more embodiments described herein.

FIG. 4A can illustrate an example, non-limiting scheme 400 that can depict the generation of one or more amine monomers (e.g., first amine monomer 402, which can be characterized by chemical formula 200) in accordance with one or more embodiments described herein (e.g., method 300). Repetitive description of like elements employed in other embodiments described herein is omitted for sake of brevity. Thus, scheme 400 can depict a generation of one or more amine monomers (e.g., first amine monomer 402, which can be characterized by chemical formula 200) in accordance with the various features of method 300. While one or more particular amine reactants (e.g., amine monomer reactant 404), aminolysis reagents, solvents, and/or catalysts are depicted; additional embodiments of scheme 400 are also envisaged. For example, the principal mechanisms of scheme 400 can be applied to any amine reactant (e.g., comprising a plurality ester groups bonded to one or more guanidium groups), aminolysis reagents, solvents, and/or catalysts in accordance with the various features described herein (e.g., with reference to chemical formula 200 and/or method 300).

As shown in FIG. 4A, scheme 400 can depict an aminolysis (e.g., in accordance with method 300) of one or more amine monomer reactants 404 (e.g., 1,3-bis(butoxycarbonyl)guanidine) with one or more aminolysis reagents (e.g., 3-(dimethylamino)-1-propylamine) to generate one or more amine monomers (e.g., first amine monomer 402, which can be characterized by chemical formula 200). For example, the one or more amine monomer reactants 404 (e.g., 1,3-bis(butoxycarbonyl)guanidine) can be dissolved with the one or more aminolysis reagent (e.g., 3-(dimethylamino)-1-propylamine) in a solvent (e.g., THF) in the presence of a catalyst (e.g., TBD). The one or more amine monomer reactants 404 (e.g., 1,3-bis(butoxycarbonyl)guanidine), the one or more aminolysis reagents (e.g., 3-(dimethylamino)-1-propylamine), the solvent (e.g., THF), and/or the catalyst (e.g., TBD) can be stirred at a temperature greater than or equal to 15° C. and less than or equal to 150° C. (e.g., 68° C.) for a period of time greater than or equal to 8 hours and less than or equal to 72 hours (e.g., greater than or equal to 12 hours and less than or equal to 24 hours).

The one or more amine monomers (e.g., first amine monomer 402, which can be characterized by chemical formula 200) can comprise a molecular backbone 102 having one or more bis(urea)guanidinium structures bonded to a first functional group 202 and/or a second functional group 204. An aminolysis (e.g., the aminolysis at 304) can replace one or more oxygens of the one or more ester groups of the one or more amine monomer reactants 404 with one or more first amino groups of the one or more aminolysis reagents (3-(dimethylamino)-1-propylamine) to form one or more urea structures, wherein the one or more second amino groups of the one or more aminolysis reagents can thereby comprise the one or more first functional groups 202 and/or second functional groups 204. The one or more first functional groups 202 and/or the one or more second functional groups 204 of the one or more amine monomers (e.g., first amine monomers 402) can have the same structure. For example, the one or more first functional groups 202 and/or the one or more second functional groups 204 can both comprise a tertiary amino group comprising the second amino group of the aminolysis reagent (e.g., 3-(dimethylamino)-1-propylamine).

Figure 4B:
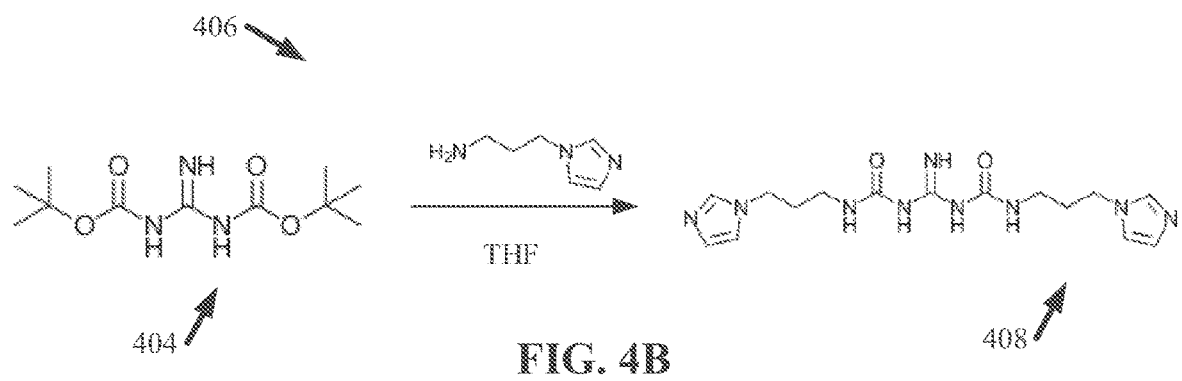
FIG. 4B illustrates another diagram of an example, non-limiting scheme that can facilitate generating one or more amine monomers in accordance with one or more embodiments described herein.

FIG. 4B can illustrate an example, non-limiting scheme 406 that can depict the generation of one or more amine monomers (e.g., second amine monomers 408, which can be characterized by chemical formula 200) in accordance with one or more embodiments described herein (e.g., method 300). Repetitive description of like elements employed in other embodiments described herein is omitted for sake of brevity. Thus, scheme 400 can depict a generation of one or more amine monomers (e.g., second amine monomers 408, which can be characterized by chemical formula 200) in accordance with the various features of method 300. While one or more particular amine reactants (e.g., amine monomer reactant 404), aminolysis reagents, and/or solvents are depicted; additional embodiments of scheme 406 are also envisaged. For example, the principal mechanisms of scheme 406 can be applied to any amine reactants (e.g., comprising a plurality ester groups bonded to one or more guanidium groups), aminolysis reagents, and/or solvents, in accordance with the various features described herein (e.g., with reference to chemical formula 200 and/or method 300).

As shown in FIG. 4B, scheme 406 can depict an aminolysis (e.g., in accordance with method 300) of one or more amine monomer reactants 404 (e.g., 1,3-bis(butoxycarbonyl)guanidine) with one or more aminolysis reagents (e.g., (3-aminopropyl)imidazole) to generate one or more amine monomers (e.g., second amine monomer 408, which can be characterized by chemical formula 200). For example, the one or more amine monomer reactants 404 (e.g., 1,3-bis (butoxycarbonyl)guanidine) can be dissolved with the one or more aminolysis reagent (e.g., (3-aminopropyl)imidazole) in a solvent (e.g., THF). The aminolysis of scheme 406 can be a self-catalyzed process. The one or more amine monomer reactants 404 (e.g., 1,3-bis(butoxycarbonyl)guanidine), the one or more aminolysis reagents (e.g., (3-aminopropyl) imidazole), and/or the solvent (e.g., THF) can be stirred at a temperature greater than or equal to 15° C. and less than or equal to 150° C. (e.g., 68° C.) for a period of time greater than or equal to 8 hours and less than or equal to 72 hours (e.g., greater than or equal to 12 hours and less than or equal to 24 hours).

The one or more amine monomers (e.g., second amine monomer 408, which can be characterized by chemical formula 200) can comprise a molecular backbone 102 having one or more bis(urea)guanidinium structures bonded to a first functional group 202 and/or a second functional group 204. An aminolysis (e.g., the aminolysis at 304) can replace one or more oxygens of the one or more ester groups of the one or more amine monomer reactants 404 with one or more first amino groups of the one or more aminolysis reagents ((3-aminopropyl)imidazole) to form one or more urea structures, wherein the one or more second amino groups of the one or more aminolysis reagents can thereby comprise the one or more first functional groups 202 and/or second functional groups 204. The one or more first functional groups 202 and/or the one or more second functional groups 204 of the one or more amine monomers (e.g., second amine monomers 408) can have the same structure. For example, the one or more first functional groups 202 and/or the one or more second functional groups 204 can both comprise an imidazole group comprising the second amino group of the aminolysis reagent (e.g., (3-aminopropyl)imidazole).

Figure 5:
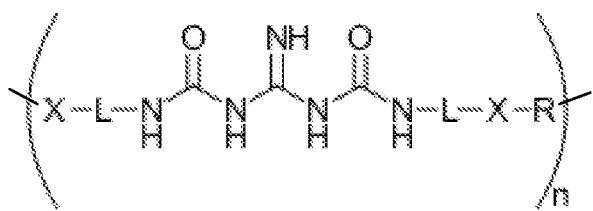
FIG. 5 illustrates a diagram of an example, non-limiting chemical formula that can characterized one or more ionene units in accordance with one or more embodiments described herein.

FIG. 5 illustrates a diagram of an example, non-limiting chemical formula 500 that can characterize the structure of an ionene unit 100 in accordance with one or more embodiments described herein. Repetitive description of like elements employed in other embodiments described herein is omitted for sake of brevity. In one or more embodiments, the ionene unit 100 characterized by chemical formula 500 can form a monomer. In various embodiments, a plurality of ionene units 100 characterized by chemical formula 500 can be covalently bond together to form a polymer (e.g., an alternating copolymer and/or a random copolymer).

As shown in FIG. 5, an ionene unit 100 characterized by chemical formula 500 can comprise a degradable molecular backbone 102. Further, the degradable molecular backbone 102 can comprise one or more bis(urea)guanidinium structures. In various embodiments, the ionene unit 100 characterized by chemical formula 500 can be derived from 1,3-bis(butoxycarbonyl)guanidine, wherein the one or more guanidinium groups can be derived from the 1,3-bis(butoxycarbonyl)guanidine. However, one or more embodiments of chemical formula 500 can comprise one or more bis(urea)guanidinium structures derived from one or more molecules other than 1,3-bis(butoxycarbonyl)guanidine.

The "X" in FIG. 5 can represent the one or more cations 104. For example, "X" can represent one or more cations 104 selected from a group that can include, but is not limited to: one or more nitrogen cations, one or more phosphorus cations, and/or a combination thereof. For instance, "X" can represent one or more nitrogen cations selected from a group that can include, but is not limited to: one or more protonated secondary amine cations, one or more protonated tertiary amine cations, one or more quaternary ammonium cations, one or more imidazolium cations, and/or a combination thereof. In another instance, "X" can represent one or more phosphorus cations selected from a group that can include, but is not limited to: one or more protonated secondary phosphine cations, one or more protonated tertiary phosphine cations, one or more quaternary phosphonium cations, and/or a combination thereof.

The one or more cations 104 (e.g., represented by "X" in chemical formula 500) can be covalently bonded to one or more linkage groups to form, at least a portion, of the degradable molecular backbone 102. The one or more linkage groups can link the one or more cations 104 to the one or more bis(urea)guanidinium structures, thereby comprising the molecular backbone 102. The "L" in FIG. 5 can represent the one or more linkage groups. The one or more linkage groups can comprise any structure in compliance with the various features of the molecular backbone 102 described herein. For example, the one or more linkage groups can have any desirable formation, including, but not limited to: chain formations, ring formations, and/or a combination thereof. The one or more linkage groups can comprise one or more chemical structures including, but not limited to: alkyl structures, aryl structures, alkane structures, aldehyde structures, ester structures, carboxyl structures, carbonyl structures, a combination thereof, and/or the like. For instance, "L" can represent one or more linkage groups that can comprise an alkyl chain having greater than or equal to two carbon atoms and less than or equal to 15 carbon atoms.

As shown in FIG. 5, in various embodiments, an ionene unit 100 characterized by chemical formula 500 can comprise cations 104 (e.g., represented by "X") at a plurality of locations along the molecular backbone 102. For example, cations 104 can be located at either end of the molecular backbone 102 (e.g., as illustrated in FIG. 5). However, in one or more embodiments of chemical formula 500, the molecular backbone 102 can comprise less or more cations 104 than the two illustrated in FIG. 5.

Further, the "R" shown in FIG. 5 can represent the one or more hydrophobic functional groups 106 in accordance with the various embodiments described herein. For example, the one or more hydrophobic functional groups 106 can comprise one or more alkyl groups and/or one or more aryl groups. For instance, the hydrophobic functional group 106 can be derived from one or more dialkyl halides. The one or more hydrophobic functional groups 106 (e.g., represented by "R" in FIG. 5) can be covalently bonded to one or more of the cations 104 (e.g., represented by "X" in FIG. 5) and/or the molecular backbone 102, which can comprise the one or more cations 104 (e.g., represented by "X" in FIG. 5), one or more linkage groups (e.g., represented by "L" in FIG. 5), and/or one or more bis(urea)guanidinium structures.

Moreover, an ionene and/or polyionene characterized by chemical formula 500 can comprise a single ionene unit 100 or a repeating ionene unit 100. For example, the "n" shown in FIG. 5 can represent a first integer greater than or equal to one and less than or equal to one thousand. Thus, an ionene unit 100 characterized by chemical formula 500 can form monomers and/or polymers (e.g., alternating copolymers and/or random copolymers).

Figure 6:
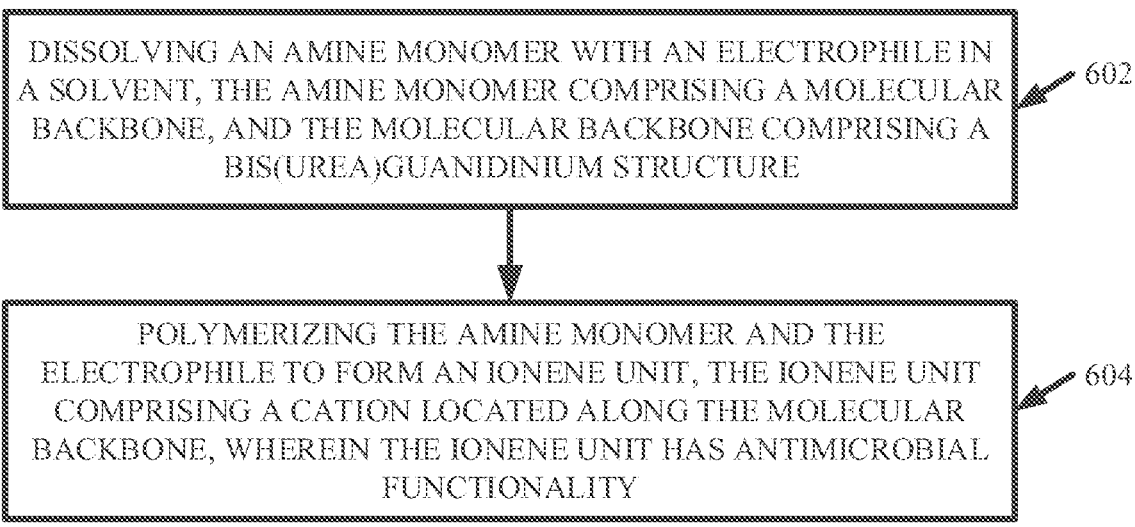
FIG. 6 illustrates a flow diagram of an example, non-limiting method that can facilitate generating one or more ionene units in accordance with one or more embodiments described herein.

FIG. 6 illustrates another flow diagram of an example, non-limiting method 600 that can generate one or more ionene units 100, which can be characterized by chemical formula 500, in accordance with one or more embodiments described herein. Repetitive description of like elements employed in other embodiments described herein is omitted for sake of brevity.

At 602, the method 600 can comprise dissolving one or more amine monomers (e.g., characterized by chemical formula 200) with one or more electrophiles in a solvent. The one or more amine monomers (e.g., characterized by chemical formula 200) can comprise a molecular backbone 102 that has one or more bis(urea)guanidinium structures. The one or more amine monomers can be degradable (e.g., biodegradable) and/or comprise one or more functional groups (e.g., first functional group 202 and/or second functional group 204), which can be ionized. The one or more amine monomers can further comprise a structure selected from a group that can include, but is not limited to: alkyl amine groups, hetero cyclic amine groups, a combination thereof, and/or the like. For example, the one or more amine monomers can be characterized by chemical formula 200 and/or generated by method 400. For instance, the one or more amine monomers can comprise first amine monomer 402 depicted in FIG. 4A and/or second amine monomer 408 depicted in FIG. 4B. In one or more embodiments, the one or more amine monomers (e.g., characterized by chemical formula 200) can be prepared using one or more techniques other than those described in regards to method 300.

The one or more electrophiles can comprise, for example, one or more alkyl halides (e.g., dialkyl halides). For instance, the one or more electrophiles can comprise one or more dialkyl halides having chloride and/or bromide. Example electrophiles can include, but are not are not limited to: p-xylylene dichloride, 4,4'-bis(chloromethyl)biphenyl; 1,4-bis(bromomethyl)benzene; 4,4'-bis(bromomethyl)biphenyl; 1,4-bis(iodomethyl)benzene; 1,6-dibromohexane; 1,8-dibromooctane; 1,12-dibromododecane; 1,6-dichlorohexane; 1,8-dichlorooctane; a combination thereof; and/or the like.

The solvent can be an organic solvent. Additionally, the solvent can be an aprotic solvent, a dipolar solvent, and/or an alcohol. Example solvents can include but are not limited to: DMF, methanol, a combination thereof, and/or the like. For example, DMF can be used as the solvent as it can dissolve the reactants at elevated temperatures. In one or more embodiments, equimolar amounts of the plurality of degradable amine monomers and the one or more electrophiles can be dissolved in the solvent.

To facilitate the dissolving at 602, the method 600 can optionally comprise stirring the one or more amine monomers, the one or more electrophiles, and the solvent at a temperature greater than or equal to 15'C and less than or equal to 150° C. for a period of time greater than or equal to 8 hours and less than or equal to 72 hours (e.g., greater than or equal to 12 hours and less than or equal to 24 hours).

Additionally, an organocatalyst can optionally be added at 602. Example, organocatalysts include, but are not limited to: 1,8-diazabicyclo[5.4.0]undec-7-ene ("DBU"), 1-(3,5-bis (trifluoromethyl)-phenyl)-3-cyclohexyl-2-thiourea ("TU"), a combination thereof, and/or the like.

At 604, the method 600 can comprise polymerizing the one or more amine monomers and the one or more electrophiles to form an ionene unit 100. The ionene unit 100 (e.g., characterized by chemical formula 500) can comprise a cation 104 distributed along a degradable molecular backbone 102. The molecular backbone 102 can comprise one or more bis(urea)guanidinium structures (e.g., as illustrated in chemical formula 500). Further, the ionene unit 100 formed at 604 can have antimicrobial functionality and/or supramolecular assembly functionality. In one or more embodiments, the polymerizing at 604 can be performed under nitrogen gas. Additionally, the polymerizing at 604 can generate the cation through alkylation and/or quaternation with the one or more electrophiles.

During the polymerization at 604, a nitrogen atom and/or a phosphorus atom located in the one or more amine monomers (e.g., comprising the first functional group 202 and/or the second functional group 204) can be subject to alkylation and/or quaternization; thus, the polymerization at 604 can conduct a polymer-forming reaction (e.g., formation of the ionene unit 100) and an installation of charge (e.g., forming a cation 104, including a nitrogen cation and/or a phosphorus cation) simultaneously without a need of a catalyst. Further, one or more hydrophobic functional groups 106 can be derived from the one or more electrophiles and/or can be bonded to the one or more cations 104 as a result of the alkylation and/or quaternization process.

For example, the ionene formed at 604 can comprise one or more embodiments of the ionene unit 100 and can be characterized by one or more embodiments of chemical formula 500. For instance, the ionene unit 100 formed at 604 can comprise a degradable molecular backbone 102 that can comprise one or more cations 104 (e.g., represented by "X" in chemical formula 500), one or more linkage groups (e.g., represented by "L" in chemical formula 500), one or more bis(urea)guanidinium structures (e.g., as shown in FIG. 5), and/or one or more hydrophobic functional groups 106 (e.g., represented by "R" in chemical formula 500). The one or more cations 104 can be nitrogen cations (e.g., protonated secondary amine cations, protonated tertiary amine cations, quaternary ammonium cations, imidazolium cations, and/or a combination thereof) and/or phosphorus cations (e.g., quaternary phosphonium cations). The cations 104 can be linked to the one or more bis(urea)guanidinium structures via one or more linkage groups (e.g., alkyl groups and/or aryl groups). Further, one or more of the cations 104 can be bonded to one or more of the hydrophobic functional groups 106. Additionally, the ionene unit 100 formed at 604 can repeat a number of times greater than or equal to 1 and less than or equal to 1000.

Antimicrobial activity of the repeating ionene units 100 generated by the methods described herein (e.g., method 600) can be independent of molecular weight. Thus, the method 600 can target polymerization conditions that can extinguish molecular weight attainment by diffusion limited mechanism (e.g., polymer precipitation) to modest molecular weights (e.g., molecular weights less than 7,000 grams per mole (g/mol)), which can aid in the solubility of the repeating ionene units 100 in aqueous media.

Figure 7A:
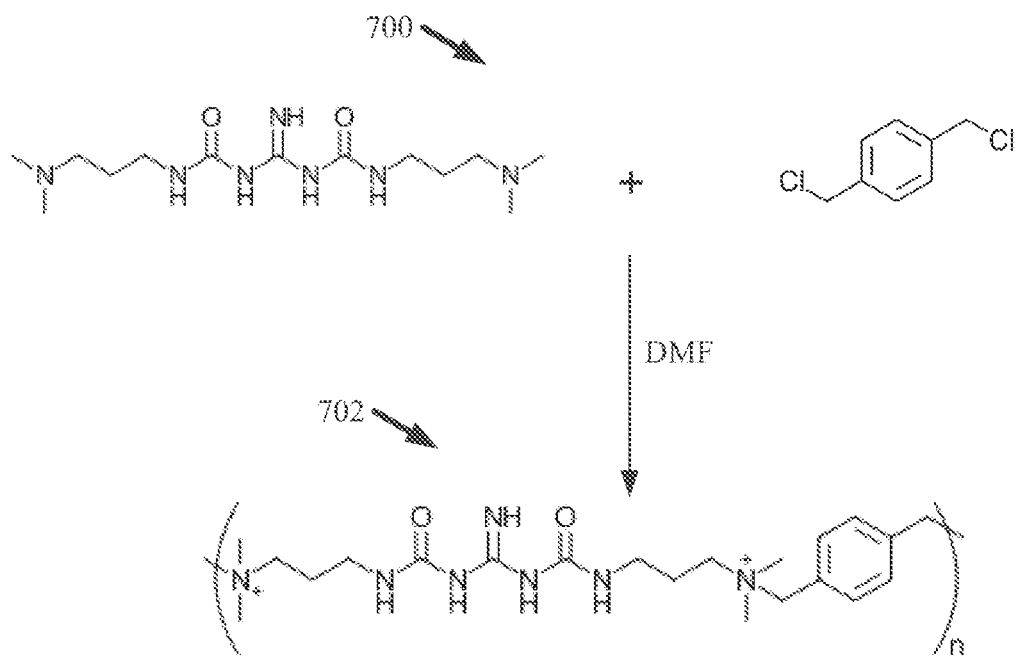
FIG. 7A illustrates a diagram of an example, non-limiting scheme that can facilitate generating one or more ionene units in accordance with one or more embodiments described herein.

FIG. 7A can illustrate an example, non-limiting scheme 700 that can depict the generation of one or more ionene compositions (e.g., first ionene composition 702, which can be characterized by chemical formula 500) in accordance with one or more embodiments described herein (e.g., method 600). Repetitive description of like elements employed in other embodiments described herein is omitted for sake of brevity. Thus, scheme 700 can depict a generation of one or more ionene compositions (e.g., first ionene composition 702 that can be characterized by chemical formula 500) in accordance with the various features of method 600. While one or more particular amine monomers, electrophiles, and/or solvents are depicted; additional embodiments of scheme 700 are also envisaged. For example, the principal mechanisms of scheme 700 can be applied to any amine monomer, electrophiles, and/or solvents in accordance with the various features described herein (e.g., with reference to chemical formula 500 and/or method 600).

As shown in FIG. 7A, scheme 700 can depict a polymerization (e.g., in accordance with method 600) of one or more amine monomers (e.g., first amine monomer 402) with one or more electrophiles (e.g., p-xylylene dichloride) to generate one or more ionene compositions (e.g., first ionene composition 702, which can be characterized by chemical formula 500). For example, the one or more amine monomers (e.g., first amine monomer 402) can be dissolved with the one or more electrophiles (e.g., p-xylylene dichloride) in a solvent (e.g., DMF). The one or more amine monomers (e.g., first amine monomer 402), the one or more electrophiles (e.g., p-xylylene dichloride), and/or the solvent (e.g., DMF) can be stirred at a temperature greater than or equal to 15° C. and less than or equal to 150° C. (e.g., 85° C.) for a period of time greater than or equal to 8 hours and less than or equal to 72 hours (e.g., greater than or equal to 12 hours and less than or equal to 24 hours).

The one or more ionene compositions (e.g., first ionene composition 702, which can be characterized by chemical formula 500) can comprise a molecular backbone 102 having one or more bis(urea)guanidinium structures. A polymerization (e.g., the polymerization at 604) can subject a functional group bonded to the molecular backbone 102 (e.g., first functional group 202 and/or second functional group 204) to a quaternization with the one or more electrophiles; thereby bonding a hydrophobic group 106 to the molecular backbone 102 and/or forming one or more cations 104. For example, in scheme 700, the quaternization can form one or more quaternary ammonium cations that can be bonded to both the molecular backbone 102 (e.g., via a linkage group) and the hydrophobic functional group 106 (e.g., derived from the one or more electrophiles). The one or more ionene compositions (e.g., first ionene composition 702) can comprise monomers and/or polymers (e.g., homopolymers, alternating copolymers, and/or random copolymers), wherein the "n" shown in FIG. 7A can represent an integer greater than or equal to one and less than or equal to one thousand.

Figure 7B:
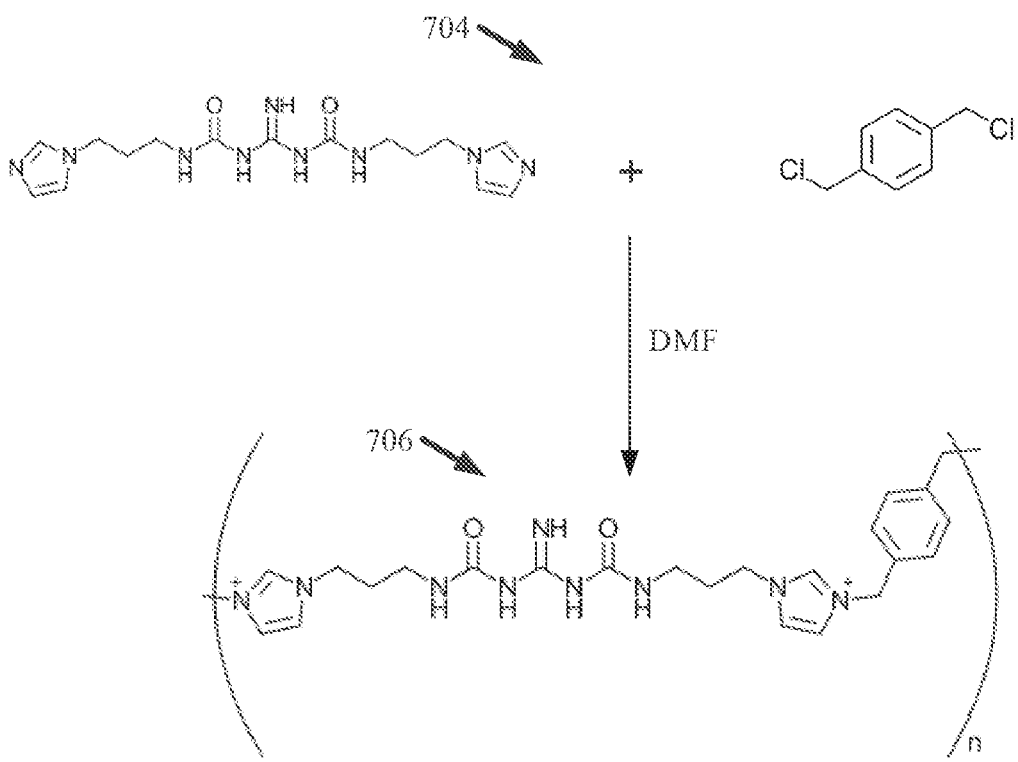
FIG. 7B illustrates another diagram of an example, non-limiting scheme that can facilitate generating one or more ionene units in accordance with one or more embodiments described herein.

FIG. 7B can illustrate an example, non-limiting scheme 704 that can depict the generation of one or more ionene compositions (e.g., first ionene composition 706, which can be characterized by chemical formula 500) in accordance with one or more embodiments described herein (e.g., method 600). Repetitive description of like elements employed in other embodiments described herein is omitted for sake of brevity. Thus, scheme 704 can depict a generation of one or more ionene compositions (e.g., first ionene composition 702 that can be characterized by chemical formula 500) in accordance with the various features of method 600. While one or more particular amine monomers, electrophiles, and/or solvents are depicted; additional embodiments of scheme 704 are also envisaged. For example, the principal mechanisms of scheme 704 can be applied to any amine monomer, electrophiles, and/or solvents in accordance with the various features described herein (e.g., with reference to chemical formula 500 and/or method 600).

As shown in FIG. 7B, scheme 704 can depict a polymerization (e.g., in accordance with method 600) of one or more amine monomers (e.g., second amine monomer 408) with one or more electrophiles (e.g., p-xylylene dichloride) to generate one or more ionene compositions (e.g., second ionene composition 706, which can be characterized by chemical formula 500). For example, the one or more amine monomers (e.g., second amine monomer 408) can be dissolved with the one or more electrophiles (e.g., p-xylylene dichloride) in a solvent (e.g., DMF). The one or more amine monomers (e.g., second amine monomer 408), the one or more electrophiles (e.g., p-xylylene dichloride), and/or the solvent (e.g., DMF) can be stirred at a temperature greater than or equal to 15° C. and less than or equal to 150° C. (e.g., 85° C.) for a period of time greater than or equal to 8 hours and less than or equal to 72 hours (e.g., greater than or equal to 12 hours and less than or equal to 24 hours).

The one or more ionene compositions (e.g., second ionene composition 706, which can be characterized by chemical formula 500) can comprise a molecular backbone 102 having one or more bis(urea)guanidinium structures. A polymerization (e.g., the polymerization at 604) can subject a functional group bonded to the molecular backbone 102 (e.g., first functional group 202 and/or second functional group 204) to an alkylation with the one or more electrophiles; thereby bonding a hydrophobic group 106 to the molecular backbone 102 and/or forming one or more cations 104. For example, in scheme 704, the alkylation can form one or more imidazolium cations that can be bonded to both the molecular backbone 102 (e.g., via a linkage group) and the hydrophobic functional group 106 (e.g., derived from the one or more electrophiles). The one or more ionene compositions (e.g., second ionene composition 706) can comprise monomers and/or polymers (e.g., homopolymers, alternating copolymers, and/or random copolymers), wherein the "n" shown in FIG. 7B can represent an integer greater than or equal to one and less than or equal to one thousand.

Figure 8:
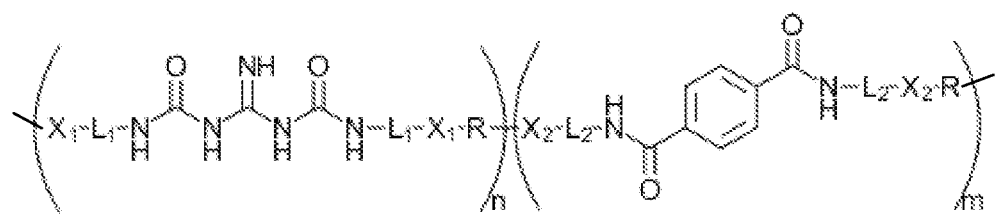
FIG. 8 illustrates a diagram of an example, non-limiting chemical formula that can characterized one or more ionene units in accordance with one or more embodiments described herein.

FIG. 8 illustrates a diagram of an example, non-limiting chemical formula 800 that can characterize the structure of one or more copolymers in accordance with one or more embodiments described herein. Repetitive description of like elements employed in other embodiments described herein is omitted for sake of brevity. In one or more embodiments, the one or more copolymers characterized by chemical formula 800 can comprise a first ionene unit 100 (e.g., characterized by chemical formula 500) covalently bonded to a second ionene unit 100. The one or more copolymers characterized by chemical formula 800 can be alternating copolymers and/or random copolymers.

As shown in FIG. 8, a first ionene unit 100 (e.g., characterized by chemical formula 500) can comprise a molecular backbone 102. Further, the molecular backbone 102 can comprise one or more bis(urea)guanidinium structures. In various embodiments, the first ionene unit 100 (e.g., characterized by chemical formula 500) can be derived from 1,3-bis(butoxycarbonyl)guanidine, wherein the one or more guanidinium groups can be derived from the 1,3-bis(butoxycarbonyl)guanidine. However, one or more embodiments of chemical formula 800 can comprise one or more bis(urea) guanidinium structures derived from one or more molecules other than 1,3-bis(butoxycarbonyl)guanidine.

The "$X_1$" in FIG. 8 can represent one or more first cations 104. For example, "$X_1$" can represent one or more first cations 104 selected from a group that can include, but is not limited to: one or more nitrogen cations, one or more phosphorus cations, and/or a combination thereof. For instance, "$X_1$" can represent one or more nitrogen cations selected from a group that can include, but is not limited to: one or more protonated secondary amine cations, one or more protonated tertiary amine cations, one or more quaternary ammonium cations, one or more imidazolium cations, and/or a combination thereof. In another instance, "$X_1$" can represent one or more phosphorus cations selected from a group that can include, but is not limited to: one or more protonated secondary phosphine cations, one or more protonated tertiary phosphine cations, one or more quaternary phosphonium cations, and/or a combination thereof.

The one or more first cations 104 (e.g., represented by "$X_1$" in chemical formula 800) can be covalently bonded to one or more first linkage groups to form, at least a portion, of the molecular backbone 102. The one or more first linkage groups can link the one or more first cations 104 to the one or more bis(urea)guanidinium structures, thereby comprising the molecular backbone 102. The "$L_1$" in FIG. 8 can represent the one or more first linkage groups. The one or more first linkage groups can comprise any structure in compliance with the various features of the molecular backbone 102 described herein. For example, the one or more first linkage groups can have any desirable formation, including, but not limited to: chain formations, ring formations, and/or a combination thereof. The one or more first linkage groups can comprise one or more chemical structures including, but not limited to: alkyl structures, aryl structures, alkane structures, aldehyde structures, ester structures, carboxyl structures, carbonyl structures, a combination thereof, and/or the like. For instance, "$L_1$" can represent one or more first linkage groups that can comprise an alkyl chain having greater than or equal to two carbon atoms and less than or equal to 15 carbon atoms.

As shown in FIG. 8, in various embodiments, one or more first ionene units 100 characterized by chemical formula 800 can comprise first cations 104 (e.g., represented by "$X_1$") at a plurality of locations along the molecular backbone 102. For example, first cations 104 can be located at either end of the molecular backbone 102 (e.g., as illustrated in FIG. 8). However, in one or more embodiments of chemical formula 800, the molecular backbone 102 can comprise less or more first cations 104 than the two illustrated in FIG. 8.

Further, the "R" shown in FIG. 8 can represent the one or more hydrophobic functional groups 106 in accordance with the various embodiments described herein. For example, the one or more hydrophobic functional groups 106 can comprise one or more alkyl groups and/or one or more aryl groups. For instance, the hydrophobic functional group 106 can be derived from one or more dialkyl halides. The one or more hydrophobic functional groups 106 (e.g., represented by "R" in FIG. 8) can be covalently bonded to one or more of the first cations 104 (e.g., represented by "$X_1$" in FIG. 8) and/or the molecular backbone 102, which can comprise the one or more first cations 104 (e.g., represented by "$X_1$" in FIG. 8), one or more first linkage groups (e.g., represented by "$L_1$" in FIG. 8), and/or one or more bis(urea)guanidinium structures.

Moreover, one or more copolymers characterized by chemical formula 800 can comprise a single first ionene unit 100 or a repeating first ionene unit 100. For example, the "n"

shown in FIG. 8 can represent a first integer greater than or equal to one and less than or equal to one thousand.

As shown in FIG. 8, the one or more copolymers that can be characterized by chemical formula 800 can further comprise a second ionene unit 100, which can comprise a degradable (e.g., biodegradable) molecular backbone 102. Further, the degradable molecular backbone 102 can comprise one or more terephthalamide structures. In various embodiments, the second ionene unit 100 (e.g., characterized by chemical formula 800) can be derived from polyethylene terephthalate ("PET"), wherein the one or more terephthalamide structures can be derived from the PET. However, one or more embodiments of chemical formula 800 can comprise one or more terephthalamide structures derived from one or more molecules other than PET.

The "$X_2$" in FIG. 8 can represent one or more second cations 104. For example, "$X_2$" can represent one or more second cations 104 selected from a group that can include, but is not limited to: one or more nitrogen cations, one or more phosphorus cations, and/or a combination thereof. For instance, "$X_2$" can represent one or more nitrogen cations selected from a group that can include, but is not limited to: one or more protonated secondary amine cations, one or more protonated tertiary amine cations, one or more quaternary ammonium cations, one or more imidazolium cations, and/or a combination thereof. In another instance, "$X_2$" can represent one or more phosphorus cations selected from a group that can include, but is not limited to: one or more protonated secondary phosphine cations, one or more protonated tertiary phosphine cations, one or more quaternary phosphonium cations, and/or a combination thereof.

The one or more second cations 104 (e.g., represented by "$X_2$" in chemical formula 800) can be covalently bonded to one or more second linkage groups to form, at least a portion, of the degradable molecular backbone 102. The one or more second linkage groups can link the one or more second cations 104 to the one or more terephthalamide structures, thereby comprising the molecular backbone 102. The "$L_2$" in FIG. 8 can represent the one or more second linkage groups. The one or more second linkage groups can comprise any structure in compliance with the various features of the molecular backbone 102 described herein. For example, the one or more second linkage groups can have any desirable formation, including, but not limited to: chain formations, ring formations, and/or a combination thereof. The one or more first linkage groups can comprise one or more chemical structures including, but not limited to: alkyl structures, aryl structures, alkenyl structures, aldehyde structures, ester structures, carboxyl structures, carbonyl structures, a combination thereof, and/or the like. For instance, "$L_2$" can represent one or more second linkage groups that can comprise an alkyl chain having greater than or equal to two carbon atoms and less than or equal to 15 carbon atoms.

As shown in FIG. 8, in various embodiments, one or more second ionene units 100 characterized by chemical formula 800 can comprise second cations 104 (e.g., represented by "$X_2$") at a plurality of locations along the degradable molecular backbone 102. For example, second cations 104 can be located at either end of the degradable molecular backbone 102 (e.g., as illustrated in FIG. 8). However, in one or more embodiments of chemical formula 800, the degradable molecular backbone 102 can comprise less or more second cations 104 than the two illustrated in FIG. 8.

Further, one or more hydrophobic functional groups 106 (e.g., represented by "R" in FIG. 8) can be covalently bonded to one or more of the second cations 104 (e.g., represented by "$X_2$" in FIG. 8) and/or the degradable molecular backbone 102, which can comprise the one or more second cations 104 (e.g., represented by "$X_2$" in FIG. 8), one or more second linkage groups (e.g., represented by "$L_2$" in FIG. 8), and/or one or more terephthalamide structures. Additionally, one or more hydrophobic functional groups 106 can be bonded to both one or more of the first cations 104 (e.g., represented by "$X_1$" in FIG. 8) of the one or more first ionene units 100 and one or more of the second cations 104 (e.g., represented by "$X_2$" in FIG. 8) of the one or more second ionene units 100; thereby bonding the one or more first ionene units 100 with the one or more second ionene units 100.

Moreover, one or more copolymers characterized by chemical formula 800 can comprise a single second ionene unit 100 or a repeating second ionene unit 100. For example, the "m" shown in FIG. 8 can represent a second integer greater than or equal to one and less than or equal to one thousand.

In one or more embodiments, the one or more first cations 104 (e.g., represented by "$X_1$") of the first ionene unit 100 can have the same structure as the one or more second cations 104 (e.g., represented by "$X_2$") of the second ionene unit 100. For example, all the cations 104 of one or more copolymers characterized by chemical formula 800, including both the one or more first cations 104 and/or the one or more second cations 104, can be quaternary ammonium cations. In another example, all the cations 104 of one or more copolymers characterized by chemical formula 800, including both the one or more first cations 104 and/or the second one or more cations 104, can be imidazolium cations. In various embodiments, the one or more first cations 104 (e.g., represented by "$X_1$") of the first ionene unit 100 can have different structures than the one or more second cations 104 (e.g., represented by "$X_2$") of the second ionene unit 100. For example, the one or more first cations 104 can be quaternary ammonium cations while the one or more second cations 104 can be imidazolium cations. In another example, the one or more first cations 104 can be imidazolium cations while the one or more second cations 104 can be quaternary ammonium cations.

Further, in one or more embodiments, the one or more first linkage groups (e.g., represented by "$L_1$") of the first ionene unit 100 can have the same structure as the one or more second linkage groups (e.g., represented by "$L_2$") of the second ionene unit 100. In some embodiments, the one or more first linkage groups (e.g., represented by "$L_1$") of the first ionene unit 100 can have different structures than the one or more second linkage groups (e.g., represented by "$L_2$") of the second ionene unit 100.

Figure 9:
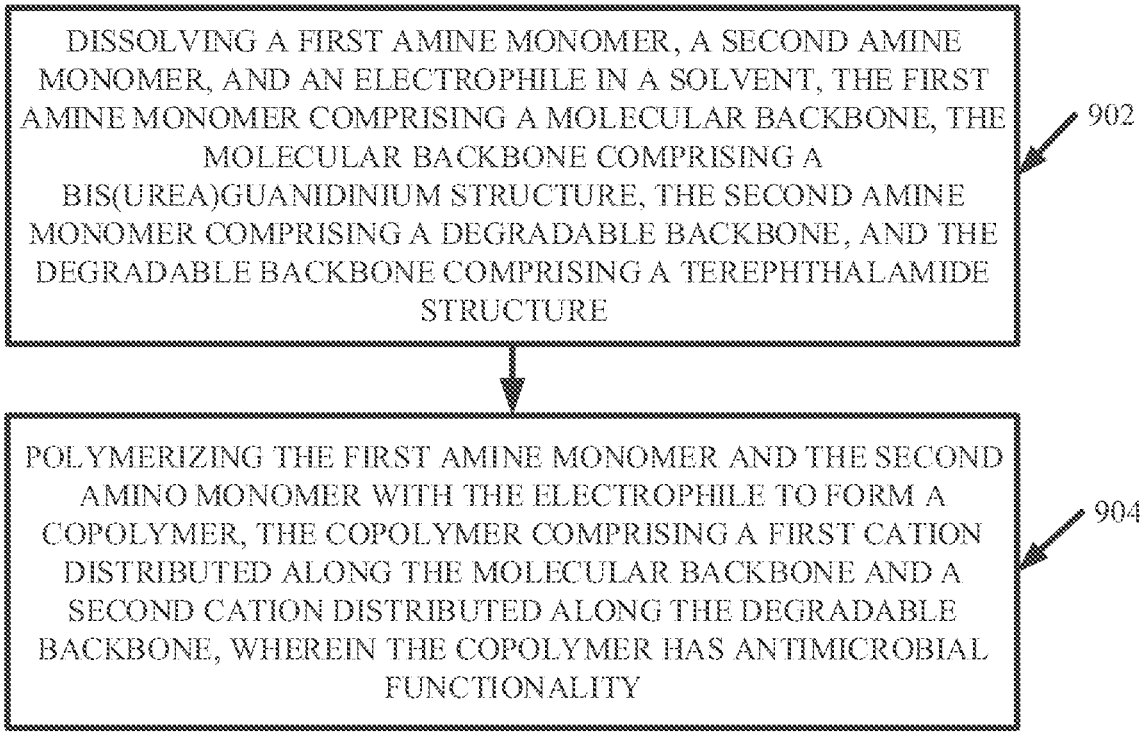
FIG. 9 illustrates a flow diagram of an example, non-limiting method that can facilitate generating one or more ionene units in accordance with one or more embodiments described herein.

FIG. 9 illustrates another flow diagram of an example, non-limiting method 900 that can generate one or more polyionenes, which can be characterized by chemical formula 800, in accordance with one or more embodiments described herein. Repetitive description of like elements employed in other embodiments described herein is omitted for sake of brevity. Method 900 can facilitate generating one or more copolymers (e.g., characterized by chemical formula 800) comprising a first ionene unit 100 and/or a second ionene unit 100. The one or more copolymers can be alternating copolymers and/or random copolymers.

At 902, the method 900 can comprise dissolving one or more first type of amine monomers (e.g., characterized by chemical formula 200) and one or more second type of amine monomers with one or more electrophiles in a solvent. The one or more first type of amine monomers (e.g., characterized by chemical formula 200) can comprise a molecular backbone 102 that has one or more bis(urea) guanidinium structures. The one or more first type of amine monomers can be degradable (e.g., biodegradable) and/or comprise one or more functional groups (e.g., first functional group 202 and/or second functional group 204), which can be ionized. The one or more first type of amine monomers can further comprise a structure selected from a group that can include, but is not limited to: alkyl amine groups, hetero cyclic amine groups, a combination thereof, and/or the like. For example, the one or more first type of amine monomers can be characterized by chemical formula 200 and/or generated by method 400. For instance, the one or more first type of amine monomers can comprise first amine monomer 402 depicted in FIG. 4A and/or second amine monomer 408 depicted in FIG. 4B. In one or more embodiments, the one or more first type of amine monomers (e.g., characterized by chemical formula 200) can be prepared using one or more techniques other than those described regarding method 300.

The one or more second type of amine monomers can comprise a degradable molecular backbone 102 that has one or more terephthalamide structures. The one or more second type of amine monomers can be degradable (e.g., biodegradable) and/or comprise one or more functional groups, which can be ionized. The one or more second type of amine monomers can further comprise a structure selected from a group that can include, but is not limited to: alkyl amine groups, hetero cyclic amine groups, a combination thereof, and/or the like. In one or more embodiments, the one or more second type of amine monomers can be tetra-amine monomers. Also, in various embodiments, the one or more second amine monomers can be derived from an aminolysis of PET.

The one or more electrophiles can comprise, for example, one or more alkyl halides (e.g., dialkyl halides). For instance, the one or more electrophiles can comprise one or more dialkyl halides having chloride and/or bromide. Example electrophiles can include, but are not are not limited to: p-xylene dichloride; 4,4'-bis(chloromethyl)biphenyl; 1,4-bis(bromomethyl)benzene; 4,4'-bis(bromomethyl)biphenyl; 1,4-bis(iodomethyl)benzene; 1,6-dibromohexane; 1,8-dibromooctane; 1,12-dibromododecane; 1,6-dichlorohexane; 1,8-dichlorooctane; a combination thereof; and/or the like. The solvent can be an organic solvent. Additionally, the solvent can be an aprotic solvent, a dipolar solvent, and/or an alcohol. Example solvents can include but are not limited to: DMF, methanol, a combination thereof, and/or the like. For example, DMF can be used as the solvent as it can dissolve the reactants at elevated temperatures.

To facilitate the dissolving at 902, the method 900 can optionally comprise stirring the one or more first type of amine monomers, the one or more second type of amine monomers, the one or more electrophiles, and the solvent at a temperature greater than or equal to 15'C and less than or equal to 150° C. for a period of time greater than or equal to 8 hours and less than or equal to 72 hours (e.g., greater than or equal to 12 hours and less than or equal to 24 hours). Additionally, an organocatlyst can optionally be added at 602. Example, organocatysts include, but are not limited to: 1,8-diazabicyclo[5.4.0]undec-7-ene ("DBU"), 1-(3,5-bis (trifluoromethyl)-phenyl)-3-cyclohexyl-2-thiourea ("TU"), a combination thereof, and/or the like.

At 904, the method 900 can comprise polymerizing the one or more first type of amine monomers and the one or more second type of amine monomers with the one or more electrophiles to form a copolymer (e.g., an alternating copolymer and/or a random copolymer). The copolymer (e.g., characterized by chemical formula 800) can comprise one or more first ionene units 100 having one or more first cations 104 distributed along a molecular backbone 102 derived from the one or more first type of amine monomers. Said molecular backbone 102 can comprise one or more bis(urea) guanidinium structures (e.g., as illustrated in chemical FIG. 8). Further, the copolymer can comprise one or more second ionene units 100 having one or more second cations 104 distributed along a degradable molecular backbone 102 derived from the one or more second type of amine monomers. Said degradable molecular backbone 102 can comprise one or more terephthalamide structures (e.g., as illustrated in FIG. 8). Additionally, the copolymer can further comprise one or more hydrophobic functional groups 106 that can be bonded to one or more first cations 104 of the one or more first ionene units 100 and/or one or more second cations 104 of the one or more second ionene units 100; thereby bonding the one or more first ionene units 100 and/or the one or more second ionene units 100 to each other.

Further, the copolymer formed at 904 can have antimicrobial functionality and/or supramolecular assembly functionality. In one or more embodiments, the polymerizing at 904 can be performed under nitrogen gas. Additionally, the polymerizing at 904 can generate the one or more first cations 104 and/or the one or more second cations 104 through alkylation and/or quaternation with the one or more electrophiles.

During the polymerization at 904, one or more nitrogen atoms and/or a phosphorus atoms located in the one or more first type of amine monomers and the one or more second type of amine monomers can be subject to alkylation and/or quaternization; thus, the polymerization at 904 can conduct a polymer-forming reaction (e.g., formation of the copolymer) and an installation of charge (e.g., forming one or more first cations 104 and/or one or more second cations 104) simultaneously without a need of a catalyst. Further, one or more hydrophobic functional groups 106 can be derived from the one or more electrophiles and/or can be bonded to the one or more first cations 104 and/or the one or more second cations 104 as a result of the alkylation and/or quaternization process.

For example, the copolymer formed at 904 can comprise a first ionene unit 100 and/or a second ionene unit 100 and/or can be characterized by one or more embodiments of chemical formula 800. For instance, the first ionene unit 100 formed at 904 can comprise a molecular backbone 102 that can comprise one or more first cations 104 (e.g., represented by "$X_1$" in chemical formula 800), one or more first linkage groups (e.g., represented by "$L_1$" in chemical formula 800), one or more bis(urea)guanidinium structures (e.g., as shown in FIG. 8), and/or one or more hydrophobic functional groups 106 (e.g., represented by "R" in chemical formula 800). The one or more first cations 104 can be nitrogen cations (e.g., protonated secondary amine cations, protonated tertiary amine cations, quaternary ammonium cations, imidazolium cations, and/or a combination thereof) and/or phosphorus cations (e.g., quaternary phosphonium cations). The one or more first cations 104 can be linked to the one or more bis(urea)guanidinium structures via one or more first linkage groups (e.g., alkyl groups and/or aryl groups). Further, one or more of the first cations 104 can be bonded to one or more of the hydrophobic functional groups 106. Additionally, the first ionene unit 100 formed at 904 can repeat a number of times greater than or equal to 1 and less than or equal to 1000.

The second ionene unit 100 formed at 904 can comprise a degradable molecular backbone 102 that can comprise one or more second cations 104 (e.g., represented by "X$_2$" in chemical formula 800), one or more second linkage groups (e.g., represented by "L$_2$" in chemical formula 800), one or more terephthalamide structures (e.g., as shown in FIG. 8), and/or one or more hydrophobic functional groups 106 (e.g., represented by "R" in chemical formula 800). The one or more second cations 104 can be nitrogen cations (e.g., protonated secondary amine cations, protonated tertiary amine cations, quaternary ammonium cations, imidazolium cations, and/or a combination thereof) and/or phosphorus cations (e.g., quaternary phosphonium cations). The one or more second cations 104 can be linked to the one or more terephthalamide structures via one or more second linkage groups (e.g., alkyl groups and/or aryl groups). Further, one or more of the second cations 104 can be bonded to one or more of the hydrophobic functional groups 106. Additionally, the second ionene unit 100 formed at 904 can repeat a number of times greater than or equal to 1 and less than or equal to 1000. Additionally, one or more hydrophobic functional groups 106 can be bonded to both one or more of the first cations 104 (e.g., represented by "X$_1$" in FIG. 8) of the one or more first ionene units 100 and one or more of the second cations 104 (e.g., represented by "X$_2$" in FIG. 8) of the one or more second ionene units 100; thereby bonding the one or more first ionene units 100 with the one or more second ionene units 100.

Antimicrobial activity of the one or more copolymers generated by the method 900 can be independent of molecular weight. Thus, the method 900 can target polymerization conditions that can extinguish molecular weight attainment by diffusion limited mechanism (e.g., polymer precipitation) to modest molecular weights (e.g., molecular weights less than 7,000 g/mol), which can aid in the solubility of the repeating ionene units 100 in aqueous media.

Figure 10A:
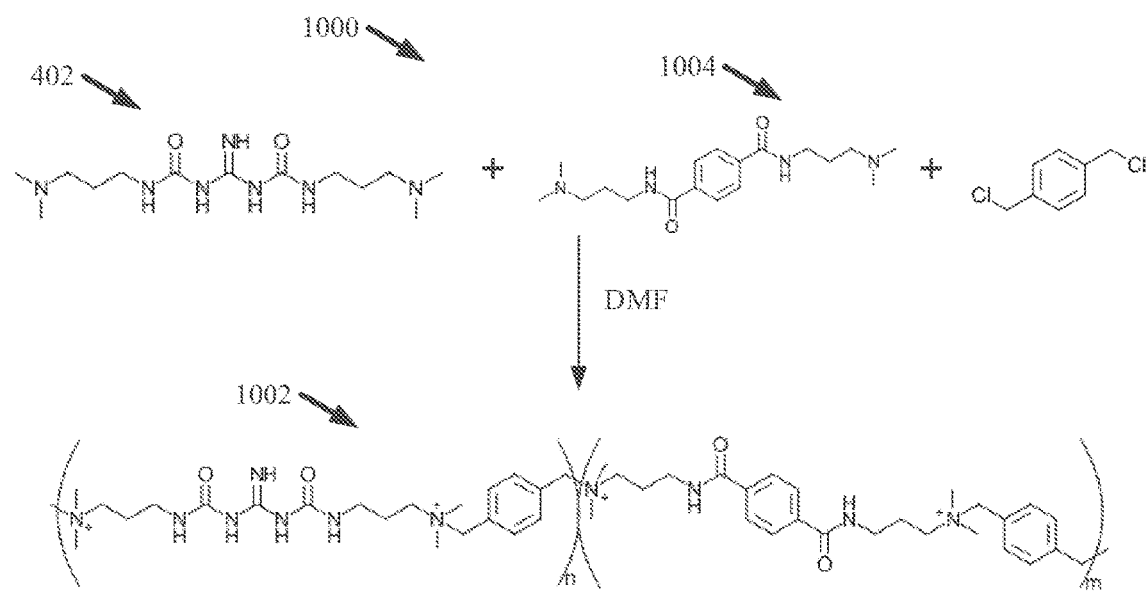
FIG. 10A illustrates a diagram of an example, non-limiting scheme that can facilitate generating one or more ionene units in accordance with one or more embodiments described herein.

FIG. 10A can illustrate an example, non-limiting scheme 1000 that can depict the generation of one or more copolymers (e.g., third ionene composition 1002, which can be characterized by chemical formula 800) in accordance with one or more embodiments described herein (e.g., method 900). Repetitive description of like elements employed in other embodiments described herein is omitted for sake of brevity. Thus, scheme 1000 can depict a generation of one or more copolymers (e.g., third ionene composition 1002 that can be characterized by chemical formula 800) in accordance with the various features of method 900. While one or more particular amine monomers, electrophiles, and/or solvents are depicted; additional embodiments of scheme 1000 are also envisaged. For example, the principal mechanisms of scheme 1000 can be applied to any amine monomer, electrophiles, and/or solvents in accordance with the various features described herein (e.g., with reference to chemical formula 800 and/or method 900).

As shown in FIG. 10A, scheme 1000 can depict a polymerization (e.g., in accordance with method 900) of one or more first monomers (e.g., first amine monomer 402) and one or more second monomers (e.g., third amine monomer 1004) with one or more electrophiles (e.g., p-xylylene dichloride) to generate one or more copolymers, which can be alternating copolymers and/or random copolymers (e.g., third ionene composition 1002, which can be characterized by chemical formula 800). For example, the one or more first monomers (e.g., first amine monomer 402) and one or more second monomers (e.g., third amine monomer 1004) can be dissolved with the one or more electrophiles (e.g., p-xylylene dichloride) in a solvent (e.g., DMF). The one or more first monomers (e.g., first amine monomer 402), the one or more second monomers (e.g., third amine monomer 1004), the one or more electrophiles (e.g., p-xylylene dichloride), and/or the solvent (e.g., DMF) can be stirred at a temperature greater than or equal to 15° C. and less than or equal to 150° C. (e.g., 85° C.) for a period of time greater than or equal to 8 hours and less than or equal to 72 hours (e.g., greater than or equal to 12 hours and less than or equal to 24 hours).

The one or more copolymers (e.g., third ionene composition 1002, which can be characterized by chemical formula 800) can comprise a first ionene unit 100 and/or a second ionene unit 100. The first ionene unit 100 can comprise a molecular backbone 102 having one or more bis(urea) guanidinium structures. A polymerization (e.g., the polymerization at 904) can subject a functional group bonded to the molecular backbone 102 (e.g., first functional group 202 and/or second functional group 204) to a quaternization with the one or more electrophiles; thereby bonding a hydrophobic group 106 to the molecular backbone 102 and/or forming one or more first cations 104. For example, in scheme 1000, the quaternization can form one or more quaternary ammonium cations that can be bonded to both the molecular backbone 102 (e.g., via a first linkage group) and the hydrophobic functional group 106 (e.g., derived from the one or more electrophiles). Also, the first ionene unit 100 can repeat a number of times greater than or equal to one and less than or equal to one thousand.

The second ionene unit 100 can comprise a degradable (e.g., biodegradable) molecular backbone 102 having one or more terephthalamide structures. A polymerization (e.g., the polymerization at 904) can subject a functional group bonded to the degradable molecular backbone 102 to a quaternization with the one or more electrophiles; thereby bonding a hydrophobic group 106 to the degradable molecular backbone 102 and/or forming one or more second cations 104. For example, in scheme 1000, the quaternization can form one or more quaternary ammonium cations that can be bonded to both the degradable molecular backbone 102 (e.g., via a second linkage group) and the hydrophobic functional group 106 (e.g., derived from the one or more electrophiles). Also, the second ionene unit 100 can repeat a number of times greater than or equal to one and less than or equal to one thousand. In addition, one or more of the first cations 104 can be bonded to the same hydrophobic functional group 106 as one or more of the second cations 104; thus, one or more common hydrophobic functional group 106 can bond the first ionene unit 100 and the second ionene unit 100 together.

Figure 10B:
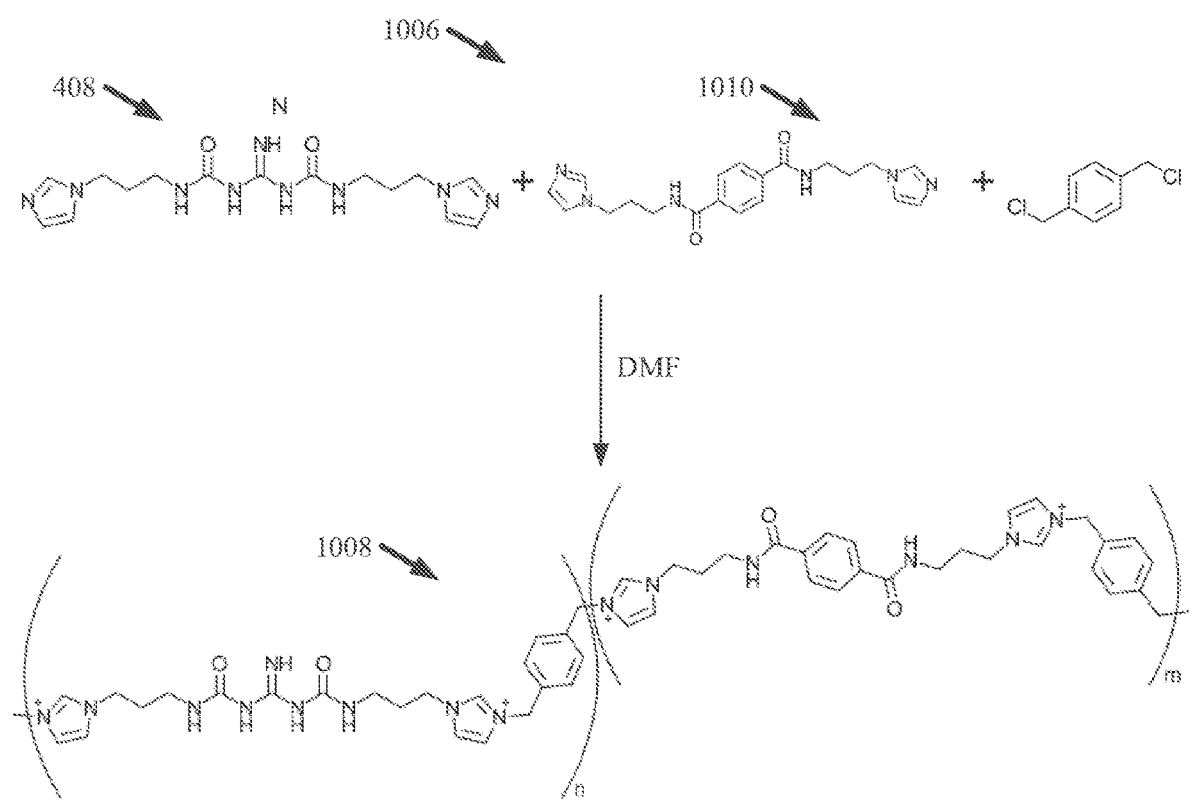
FIG. 10B illustrates another diagram of an example, non-limiting scheme that can facilitate generating one or more ionene units in accordance with one or more embodiments described herein.

FIG. 10B can illustrate an example, non-limiting scheme 1006 that can depict the generation of one or more copolymers (e.g., fourth ionene composition 1008, which can be characterized by chemical formula 800) in accordance with one or more embodiments described herein (e.g., method 900). Repetitive description of like elements employed in other embodiments described herein is omitted for sake of brevity. Thus, scheme 1006 can depict a generation of one or more copolymers (e.g., fourth ionene composition 1008 that can be characterized by chemical formula 800) in accordance with the various features of method 900. While one or more particular amine monomers, electrophiles, and/or solvents are depicted, additional embodiments of scheme 1006 are also envisaged. For example, the principal mechanisms of scheme 1006 can be applied to any amine monomer, electrophiles, and/or solvents in accordance with the various features described herein (e.g., with reference to chemical formula 800 and/or method 900).

As shown in FIG. 10B, scheme 1006 can depict a polymerization (e.g., in accordance with method 900) of one or more first monomers (e.g., second amine monomer 408) and one or more second monomers (e.g., fourth amine monomer 1010) with one or more electrophiles (e.g., p-xylylene dichloride) to generate one or more copolymers, which can be alternating copolymers and/or random copolymers (e.g., fourth ionene composition 1008, which can be characterized by chemical formula 800). For example, the one or more first monomers (e.g., second amine monomer 408) and one or more second monomers (e.g., fourth amine monomer 1010) can be dissolved with the one or more electrophiles (e.g., p-xylylene dichloride) in a solvent (e.g., DMF). The one or more first monomers (e.g., second amine monomer 408), the one or more second monomers (e.g., fourth amine monomer 1010), the one or more electrophiles (e.g., p-xylylene dichloride), and/or the solvent (e.g., DMF) can be stirred at a temperature greater than or equal to 15° C. and less than or equal to 150° C. (e.g., 85° C.) for a period of time greater than or equal to 8 hours and less than or equal to 72 hours (e.g., greater than or equal to 12 hours and less than or equal to 24 hours).

The one or more copolymers (e.g., fourth ionene composition 1008, which can be characterized by chemical formula 800) can comprise a first ionene unit 100 and/or a second ionene unit 100. The first ionene unit 100 can comprise a molecular backbone 102 having one or more bis(urea) guanidinium structures. A polymerization (e.g., the polymerization at 904) can subject a functional group bonded to the molecular backbone 102 (e.g., first functional group 202 and/or second functional group 204) to an alkylation with the one or more electrophiles; thereby bonding a hydrophobic group 106 to the molecular backbone 102 and/or forming one or more first cations 104. For example, in scheme 1006, the alkylation can form one or more imidazolium cations that can be bonded to both the molecular backbone 102 (e.g., via a first linkage group) and the hydrophobic functional group 106 (e.g., derived from the one or more electrophiles). Also, the first ionene unit 100 can repeat a number of times greater than or equal to one and less than or equal to one thousand.

The second ionene unit 100 can comprise a degradable (e.g., biodegradable) molecular backbone 102 having one or more terephthalamide structures. A polymerization (e.g., the polymerization at 904) can subject a functional group bonded to the degradable molecular backbone 102 to an alkylation with the one or more electrophiles; thereby bonding a hydrophobic group 106 to the degradable molecular backbone 102 and/or forming one or more second cations 104. For example, in scheme 1006, the alkylation can form one or more imidazolium cations that can be bonded to both the degradable molecular backbone 102 (e.g., via a second linkage group) and the hydrophobic functional group 106 (e.g., derived from the one or more electrophiles). Also, the second ionene unit 100 can repeat a number of times greater than or equal to one and less than or equal to one thousand. In addition, one or more of the first cations 104 can be bonded to the same hydrophobic functional group 106 as one or more of the second cations 104; thus, one or more common hydrophobic functional group 106 can bond the first ionene unit 100 and the second ionene unit 100 together.

Figure 11:
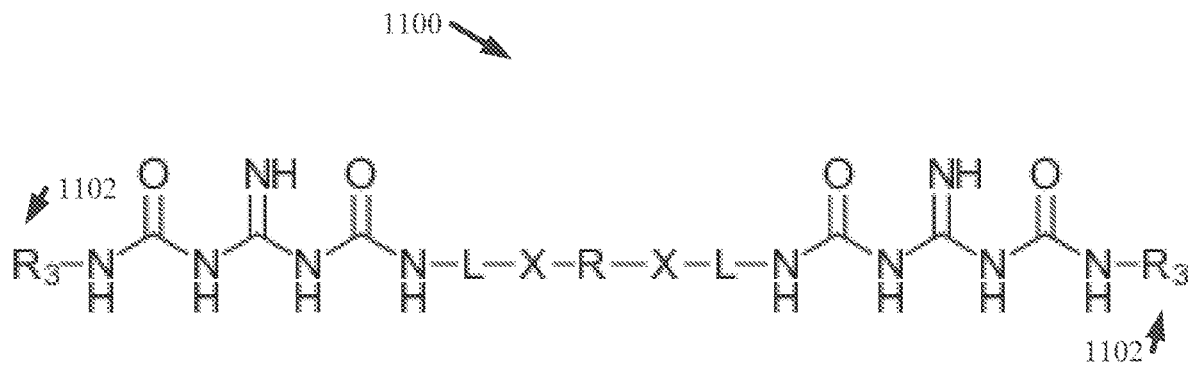
FIG. 11 illustrates a diagram of an example, non-limiting chemical formula that can characterized one or more ionene units in accordance with one or more embodiments described herein.

FIG. 11 illustrates a diagram of an example, non-limiting chemical formula 1100 that can characterize the structure of an ionene unit 100 in accordance with one or more embodiments described herein. Repetitive description of like elements employed in other embodiments described herein is omitted for sake of brevity. In one or more embodiments, the ionene unit 100 characterized by chemical formula 1100 can form a monomer. In various embodiments, a plurality of ionene units 100 characterized by chemical formula 500 can be covalently bond together to form a polymer (e.g., an alternating copolymer and/or a random copolymer).

As shown in FIG. 11, an ionene unit 100 characterized by chemical formula 1100 can comprise a degradable molecular backbone 102. Further, the degradable molecular backbone 102 can comprise a plurality of bis(urea)guanidinium structures. In various embodiments, the ionene unit 100 characterized by chemical formula 1100 can be derived from 1,3-bis(butoxycarbonyl)guanidine, wherein the plurality of guanidinium groups can be derived from the 1,3-bis(butoxycarbonyl)guanidine. However, one or more embodiments of chemical formula 1100 can comprise a plurality of bis(urea)guanidinium structures derived from one or more molecules other than 1,3-bis(butoxycarbonyl)guanidine.

The "X" in FIG. 11 can represent the one or more cations 104. For example, "X" can represent one or more cations 104 selected from a group that can include, but is not limited to: one or more nitrogen cations, one or more phosphorus cations, and/or a combination thereof. For instance, "X" can represent one or more nitrogen cations selected from a group that can include, but is not limited to: one or more protonated secondary amine cations, one or more protonated tertiary amine cations, one or more quaternary ammonium cations, one or more imidazolium cations, and/or a combination thereof. In another instance, "X" can represent one or more phosphorus cations selected from a group that can include, but is not limited to: one or more protonated secondary phosphine cations, one or more protonated tertiary phosphine cations, one or more quaternary phosphonium cations, and/or a combination thereof.

The one or more cations 104 (e.g., represented by "X" in chemical formula 1100) can be covalently bonded to one or more linkage groups to form, at least a portion, of the degradable molecular backbone 102. The one or more linkage groups can link the one or more cations 104 to the plurality of bis(urea)guanidinium structures, thereby comprising the molecular backbone 102. The "L" in FIG. 11 can represent the one or more linkage groups. The one or more linkage groups can comprise any structure in compliance with the various features of the molecular backbone 102 described herein. For example, the one or more linkage groups can have any desirable formation, including, but not limited to: chain formations, ring formations, and/or a combination thereof. The one or more linkage groups can comprise one or more chemical structures including, but not limited to: alkyl structures, aryl structures, alkenyl structures, aldehyde structures, ester structures, carboxyl structures, carbonyl structures, a combination thereof, and/or the like. For instance, "L" can represent one or more linkage groups that can comprise an alkyl chain having greater than or equal to two carbon atoms and less than or equal to 15 carbon atoms.

As shown in FIG. 11, in various embodiments, an ionene unit 100 characterized by chemical formula 1100 can comprise cations 104 (e.g., represented by "X") at a plurality of locations along the molecular backbone 102. For example, cations 104 can be located at one or more central portions of the molecular backbone 102 (e.g., as shown in FIG. 11I). However, in one or more embodiments of chemical formula 1100, the molecular backbone 102 can comprise less or more cations 104 than the two illustrated in FIG. 11.

As shown in FIG. 11, "$R_3$" can represent a third functional group 1102 covalently bonded to a plurality of the bis(urea) guanidium structures. One or more third functional group 1102 can comprise one or more ester groups and/or one or more carboxyl groups. For example, the third functional group 1102 can comprise one or more ester groups, which can comprise one or more alkyl groups and/or one or more aryl groups. Thus, the third functional group 1102 can contribute degradability to the molecular backbone 102 of the one or more amine monomers characterized by chemical formula 1100. Additionally, the third functional group 1102 can facilitate in membrane targeting and control of hydrophobicity and/or hydrophilicity of the subject one or more amine monomers.

Further, the "R" shown in FIG. 11 can represent the one or more hydrophobic functional groups 106 in accordance with the various embodiments described herein. For example, the one or more hydrophobic functional groups 106 can comprise one or more alkyl groups and/or one or more aryl groups. For instance, the hydrophobic functional group 106 can be derived from one or more dialkyl halides. The one or more hydrophobic functional groups 106 (e.g., represented by "R" in FIG. 11) can be covalently bonded to one or more of the cations 104 (e.g., represented by "X" in FIG. 11) and/or the molecular backbone 102, which can comprise the one or more cations 104 (e.g., represented by "X" in FIG. 11), one or more linkage groups (e.g., represented by "L" in FIG. 1), and/or a plurality of bis(urea) guanidinium structures.

FIG. 12 illustrates another flow diagram of an example, non-limiting method 1200 that can generate one or more ionene units 100, which can be characterized by chemical formula 1100, in accordance with one or more embodiments described herein. Repetitive description of like elements employed in other embodiments described herein is omitted for sake of brevity.

At 1202, the method 1200 can comprise dissolving one or more amine monomers (e.g., characterized by chemical formula 200) with one or more electrophiles in a solvent. The one or more amine monomers (e.g., characterized by chemical formula 200) can comprise a molecular backbone 102 that has one or more bis(urea)guanidinium structures. The one or more amine monomers can be degradable (e.g., biodegradable) and/or comprise one or more functional groups (e.g., first functional group 202 and/or second functional group 204). The first functional group 202 can be an ester group and/or a carboxyl group. For example, the first functional group 202 can comprise an ester group with an alkyl chain and/or aryl ring. The second functional group 204 can comprise an amino group and/or a phosphine group, either of which can be ionized to form one or more cations 104. The one or more amine monomers can further comprise a structure selected from a group that can include, but is not limited to: alkyl amine groups, hetero cyclic amine groups, a combination thereof, and/or the like. For example, the one or more amine monomers can be characterized by chemical formula 200 and/or generated by method 400. In one or more embodiments, the one or more amine monomers (e.g., characterized by chemical formula 200) can be prepared using one or more techniques other than those described regarding method 300.

The one or more electrophiles can comprise, for example, one or more alkyl halides (e.g., dialkyl halides). For instance, the one or more electrophiles can comprise one or more dialkyl halides having chloride and/or bromide. Example electrophiles can include, but are not limited to: p-xylylene dichloride, 4,4'-bis(chloromethyl)biphenyl; 1,4-bis(bromomethyl)benzene; 4,4'-bis(bromomethyl)biphenyl; 1,4-bis(iodomethyl)benzene; 1,6-dibromohexane; 1,8-dibromooctane; 1,12-dibromododecane; 1,6-dichlorohexane; 1,8-dichlorooctane; a combination thereof; and/or the like.

The solvent can be an organic solvent. Additionally, the solvent can be an aprotic solvent, a dipolar solvent, and/or an alcohol. Example solvents can include but are not limited to: DMF, methanol, a combination thereof, and/or the like. For example, DMF can be used as the solvent as it can dissolve the reactants at elevated temperatures. In one or more embodiments, equimolar amounts of the plurality of degradable amine monomers and the one or more electrophiles can be dissolved in the solvent.

To facilitate the dissolving at 1202, the method 1200 can optionally comprise stirring the one or more amine monomers, the one or more electrophiles, and the solvent at a temperature greater than or equal to 15° C. and less than or equal to 150° C. for a period of time greater than or equal to 8 hours and less than or equal to 72 hours (e.g., greater than or equal to 12 hours and less than or equal to 24 hours). Additionally, an organocatalyst can optionally be added at 1202. Example, organocatalysts include, but are not limited to: 1,8-diazabicyclo[5.4.0]undec-7-ene ("DBU"), 1-(3,5-bis(trifluoromethyl)-phenyl)-3-cyclohexyl-2-thiourea ("TU"), a combination thereof, and/or the like.

At 1204, the method 1200 can comprise polymerizing the one or more amine monomers and the one or more electrophiles to form an ionene unit 100. The ionene unit 100 (e.g., characterized by chemical formula 1100) can comprise a cation 104 distributed along a degradable molecular backbone 102. The molecular backbone 102 can comprise a plurality of bis(urea)guanidinium structures (e.g., as illustrated in chemical formula 1100). Further, the ionene unit 100 formed at 1104 can have antimicrobial functionality and/or supramolecular assembly functionality. In one or more embodiments, the polymerizing at 1104 can be performed under nitrogen gas. Additionally, the polymerizing at 1104 can generate the cation through alkylation and/or quaternation with the one or more electrophiles.

During the polymerization at 1104, a nitrogen atom and/or a phosphorus atom located in the one or more amine monomers (e.g., comprising the second functional group 204) can be subject to alkylation and/or quaternization; thus, the polymerization at 1104 can conduct a polymer-forming reaction (e.g., formation of the ionene unit 100) and an installation of charge (e.g., forming a cation 104, including a nitrogen cation and/or a phosphorus cation) simultaneously without a need of a catalyst. Further, one or more hydrophobic functional groups 106 can be derived from the one or more electrophiles and/or can be bonded to the one or more cations 104 as a result of the alkylation and/or quaternization process.

The ionene unit 100 (e.g., characterized by chemical formula 1100) formed by method 1200 can be an ionene monomer. For example, the polymerization at 1104 can bond two amine monomers (e.g., characterized by chemical formula 200) together via one or more hydrophobic functional groups 106, wherein the second functional groups 204 of each amine monomer are alkylized and/or quaternized with the one or more electrophiles to form one or more linkage groups, one or more cations 104, and/or one or more hydrophobic functional groups 106. The first functional groups 202 of the amine monomers can be ester groups and/or carboxyl groups and thereby constitute the third functional groups 1102 in the ionene unit 100 formed at 1204.

For example, the ionene formed at 1204 can comprise one or more embodiments of the ionene unit 100 and can be characterized by one or more embodiments of chemical formula 1100. For instance, the ionene unit 100 formed at 1204 can comprise a degradable molecular backbone 102 that can comprise one or more cations 104 (e.g., represented by "X" in chemical formula 1100), one or more linkage groups (e.g., represented by "L" in chemical formula 1100), a plurality of bis(urea)guanidinium structures (e.g., as shown in FIG. 11), one or more hydrophobic functional groups 106 (e.g., represented by "R" in chemical formula 1100), and/or one or more third functional groups 1102. The one or more cations 104 can be nitrogen cations (e.g., protonated secondary amine cations, protonated tertiary amine cations, quaternary ammonium cations, imidazolium cations, and/or a combination thereof) and/or phosphorus cations (e.g., quaternary phosphonium cations). The cations 104 can be linked to the plurality of bis(urea)guanidinium structures via one or more linkage groups (e.g., alkyl groups and/or aryl groups). Further, one or more of the cations 104 can be bonded to one or more of the hydrophobic functional groups 106. Additionally, the one or more third functional groups 1102 can comprise one or more ester groups and/or carboxyl groups, which can provide additional degradability to the ionene unit 100.

Antimicrobial activity of the repeating ionene units 100 generated by the methods described herein (e.g., method 1200) can be independent of molecular weight. Thus, the method 1200 can target polymerization conditions that can extinguish molecular weight attainment by diffusion limited mechanism (e.g., polymer precipitation) to modest molecular weights (e.g., molecular weights less than 7,000 g/mol), which can aid in the solubility of the repeating ionene units 100 in aqueous media.

Figure 13:
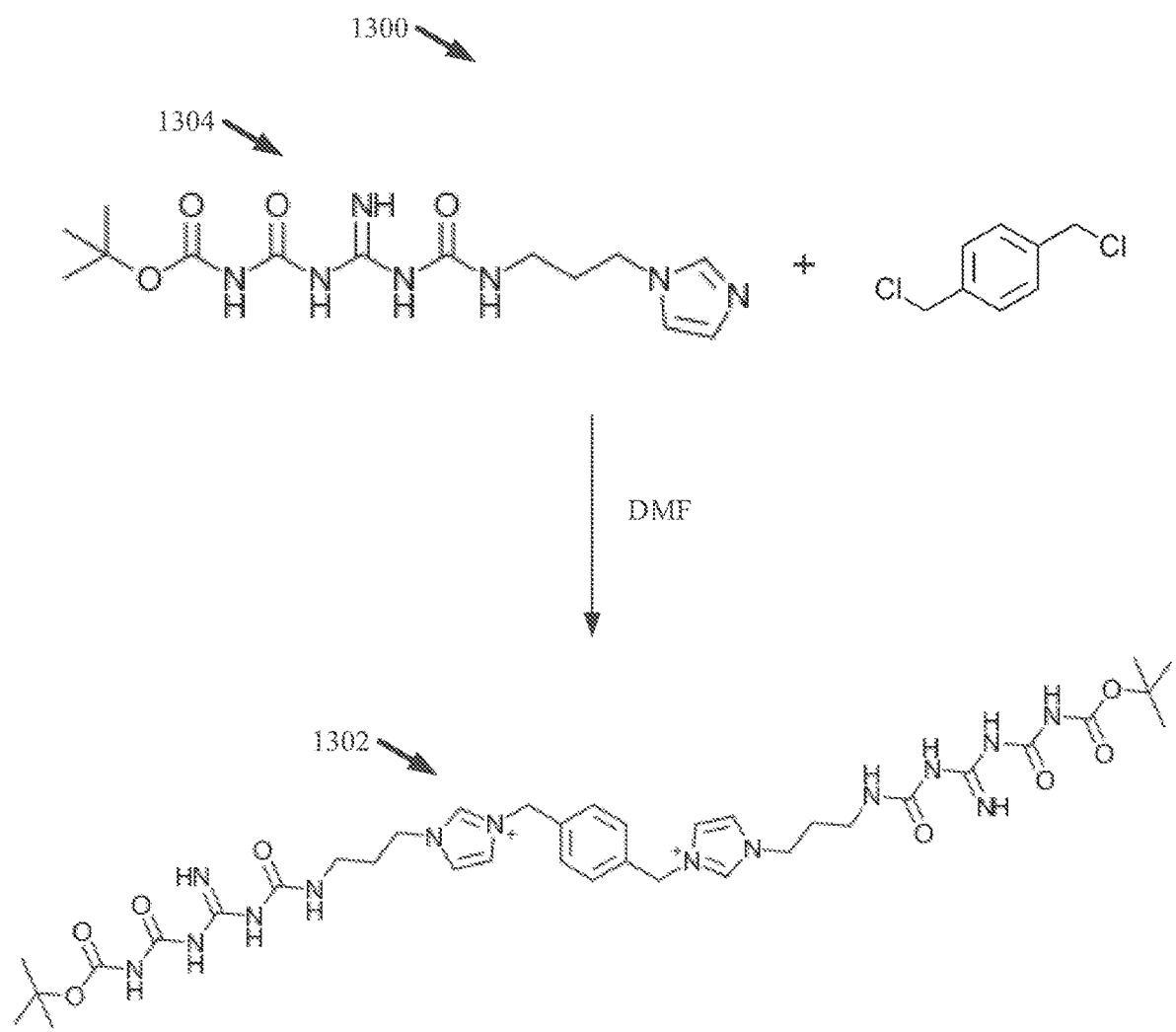
FIG. 13 illustrates a diagram of an example, non-limiting scheme that can facilitate generating one or more ionene units in accordance with one or more embodiments described herein.

FIG. 13 can illustrate an example, non-limiting scheme 1300 that can depict the generation of one or more ionene compositions (e.g., fifth ionene composition 1302, which can be characterized by chemical formula 1100) in accordance with one or more embodiments described herein (e.g., method 1200). Repetitive description of like elements employed in other embodiments described herein is omitted for sake of brevity. Thus, scheme 1300 can depict a generation of one or more ionene compositions (e.g., fifth ionene composition 1302 that can be characterized by chemical formula 1100) in accordance with the various features of method 1200. While one or more particular amine monomers, electrophiles, and/or solvents are depicted; additional embodiments of scheme 1300 are also envisaged. For example, the principal mechanisms of scheme 1300 can be applied to any amine monomer, electrophiles, and/or solvents in accordance with the various features described herein (e.g., with reference to chemical formula 1100 and/or method 1200).

As shown in FIG. 13, scheme 1300 can depict a polymerization (e.g., in accordance with method 1200) of one or more amine monomers (e.g., fifth amine monomer 1304) with one or more electrophiles (e.g., p-xylene dichloride) to generate one or more ionene compositions (e.g., fifth ionene composition 1302, which can be characterized by chemical formula 1100). For example, fifth amine monomer 1304 can be characterized by chemical formula 200, wherein the first functional group 202 can be an ester group comprising an first alkylation alkyl group and/or an aryl group. The one or more amine monomers (e.g., fifth amine monomer 1304) can be dissolved with the one or more electrophiles (e.g., p-xylylene dichloride) in a solvent (e.g., DMF). The one or more amine monomers (e.g., fifth amine monomer 1304), the one or more electrophiles (e.g., p-xylylene dichloride), and/or the solvent (e.g., DMF) can be stirred at a temperature greater than or equal to 15° C. and less than or equal to 150° C. (e.g., 85° C.) for a period of time greater than or equal to 8 hours and less than or equal to 72 hours (e.g., greater than or equal to 12 hours and less than or equal to 24 hours).

The one or more ionene compositions (e.g., fifth ionene composition 1302, which can be characterized by chemical formula 1100) can comprise a molecular backbone 102 having a plurality of bis(urea)guanidinium structures. A polymerization (e.g., the polymerization at 1204) can subject a functional group bonded to the molecular backbone 102 of the one or more amine monomers (e.g., second functional group 204) to an alkylation with the one or more electrophiles; thereby bonding a hydrophobic group 106 to the molecular backbone 102 and/or forming one or more cations 104. For example, in scheme 1300, the alkylation can form one or more imidazole cations that can be bonded to both the molecular backbone 102 (e.g., via a linkage group) and the hydrophobic functional group 106 (e.g., derived from the one or more electrophiles). The one or more ionene compositions (e.g., fifth ionene composition 1302) can comprise can be a monomer.

FIG. 14 illustrates a diagram of an example, non-limiting chart 1400 that can depict the antimicrobial efficacy of one or more ionene compositions in accordance with one or more embodiments described herein. Repetitive description of like elements employed in other embodiments described herein is omitted for sake of brevity. To demonstrate the antimicrobial effects of the ionenes described herein (e.g., ionene units 100 that can be characterized by chemical formula 200, 500, 800, and/or 1100 and/or generated by method 300, 600, 900, and/or 1200, such as those depicted in scheme 400, 700, 1000, and/or 1300), a plurality of ionene compositions were evaluated against a broad spectrum of pathogens.

The first column 1402 of chart 1400 can depict the ionene composition subject to evaluation. The second column 1404 of chart 1400 can depict the minimum inhibitory concentration (MIC) in micrograms per milliliter (μg/mL) of the subject ionene composition regarding *Staphylococcus aureus* ("SA"). The third column 1406 of chart 1400 can depict the MIC in μg/mL of the subject ionene composition regarding *Escherichia coli* ("EC"). The fourth column 1408 of chart 1400 can depict the MIC in μg/mL of the subject polyionene composition regarding *Pseudomonas aeruginosa* ("PA"). The fifth column 1410 of chart 1400 can depict the MIC in μg/mL of the subject polyionene composition regarding *Candida albicans* ("CA"). The sixth column 1412 of chart 1400 can depict the hemolytic activity ("$HC_{50}$") in μg/mL of the subject polyionene composition regarding rat red blood cells.

Figure 15:
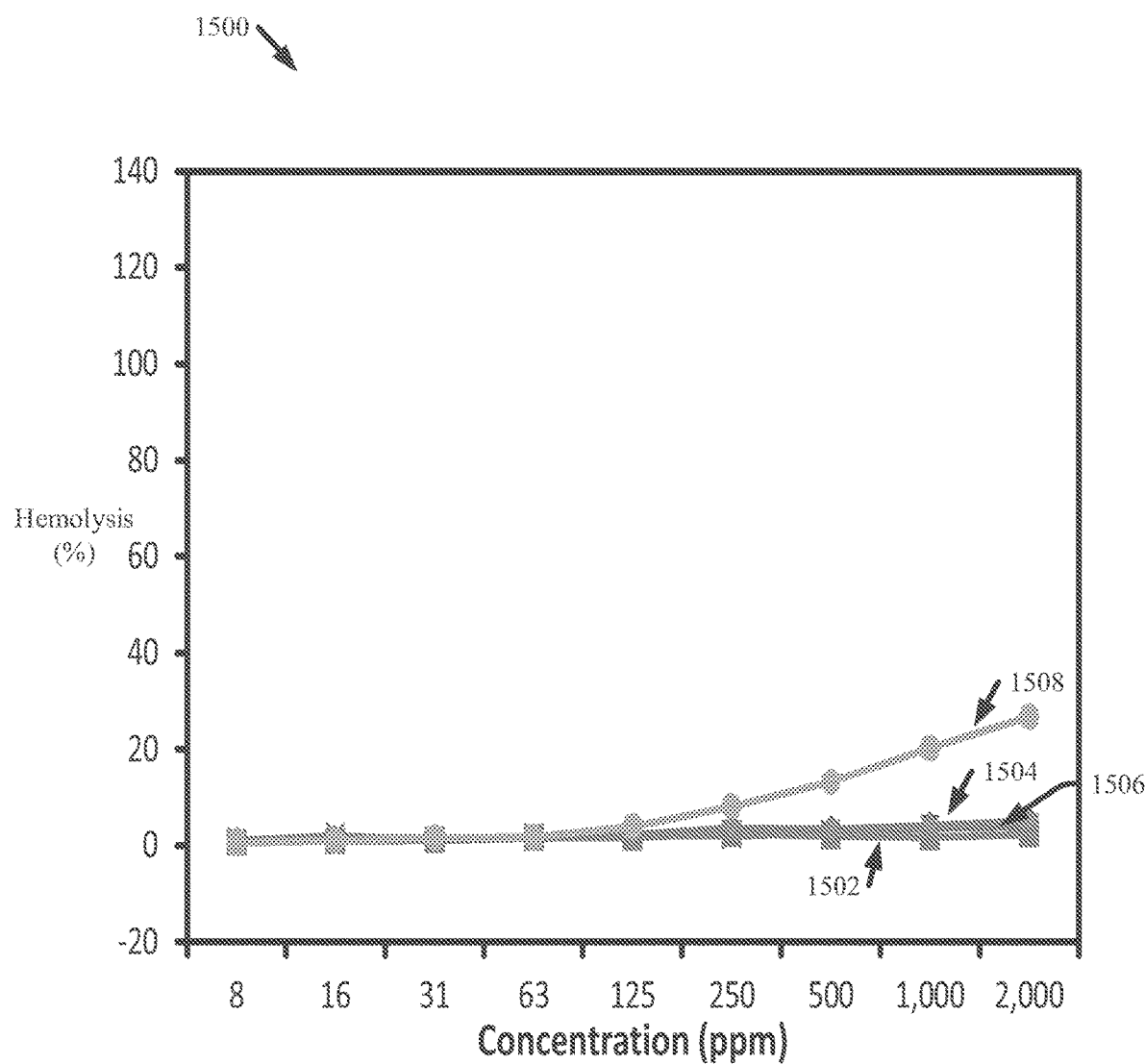
FIG. 15 illustrates a diagram of an example, non-limiting graph that can depict hemolysis activity of various ionene compositions in accordance with one or more of the embodiments described herein.

FIG. 15 illustrates a diagram of an example, non-limiting graph 1500 that can depict the hemolytic activity of various polyionene compositions at various concentrations in accordance with the one or more embodiments described herein. Repetitive description of like elements employed in other embodiments described herein is omitted for sake of brevity. For example, FIG. 15 shows the hemolytic activity of the first ionene composition 702 (e.g., depicted by line 1502), the second ionene composition 706 (e.g., depicted by line 1504), the third ionene composition 1002 (e.g., depicted by line 1506), and/or the fourth ionene composition 1006 (e.g., depicted by line 1508) at concentrations ranging from 8 parts per million (ppm) to 2000 ppm. The hemolytic activity depicted in graph 1500 can regard rat red blood cells. As shown in FIG. 15, the second ionene composition 706 and/or the third ionene composition 1002 have very similar hemolytic activity.

Figure 16A:
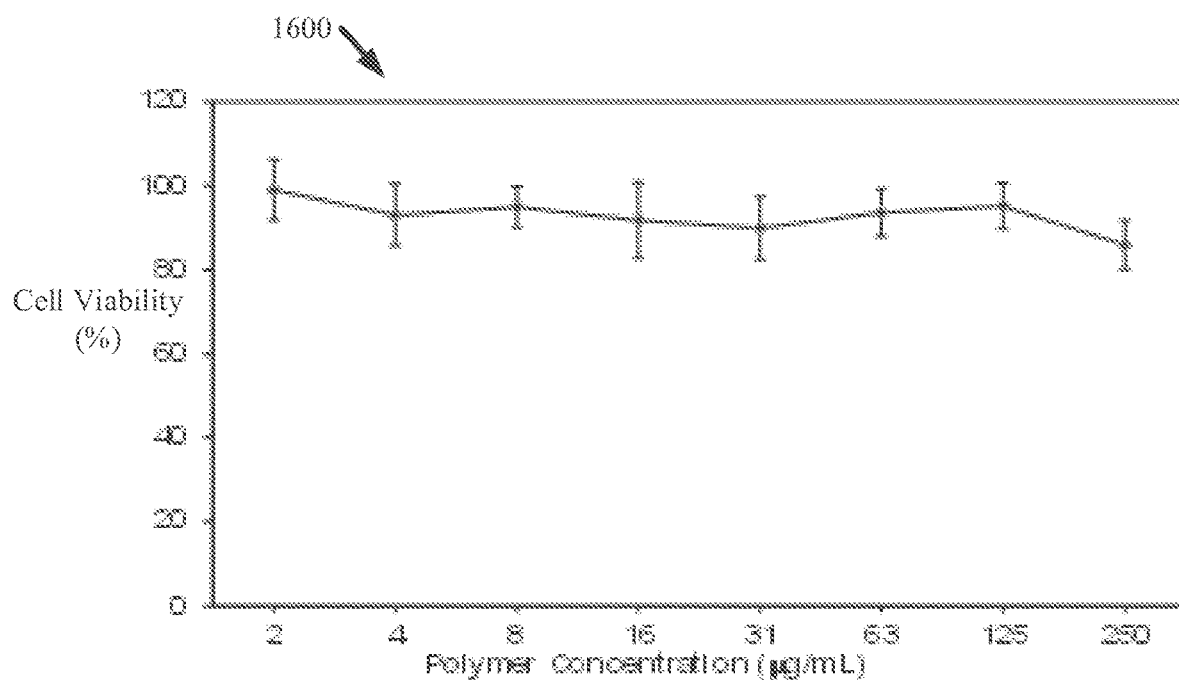
FIG. 16A illustrates a diagram of an example, non-limiting graph that can depict cell viability of an ionene composition in accordance with one or more embodiments described herein.

FIG. 16A illustrates a diagram of an example, non-limiting graph 1600 that can depict the cell viability of the fifth ionene composition 1302. Repetitive description of like elements employed in other embodiments described herein is omitted for sake of brevity. Graph 1600 shows the viability of a L929 mouse fibroblast cell line after 48 hours of incubation at 37° C. with the fifth ionene composition 1302 at various concentrations. Cell viability was determined through a 3-(4,5-dimethylthiazol-2-yl)-2,5-diphenyltetrazolium bromide (MTT) assay.

Figure 16B:
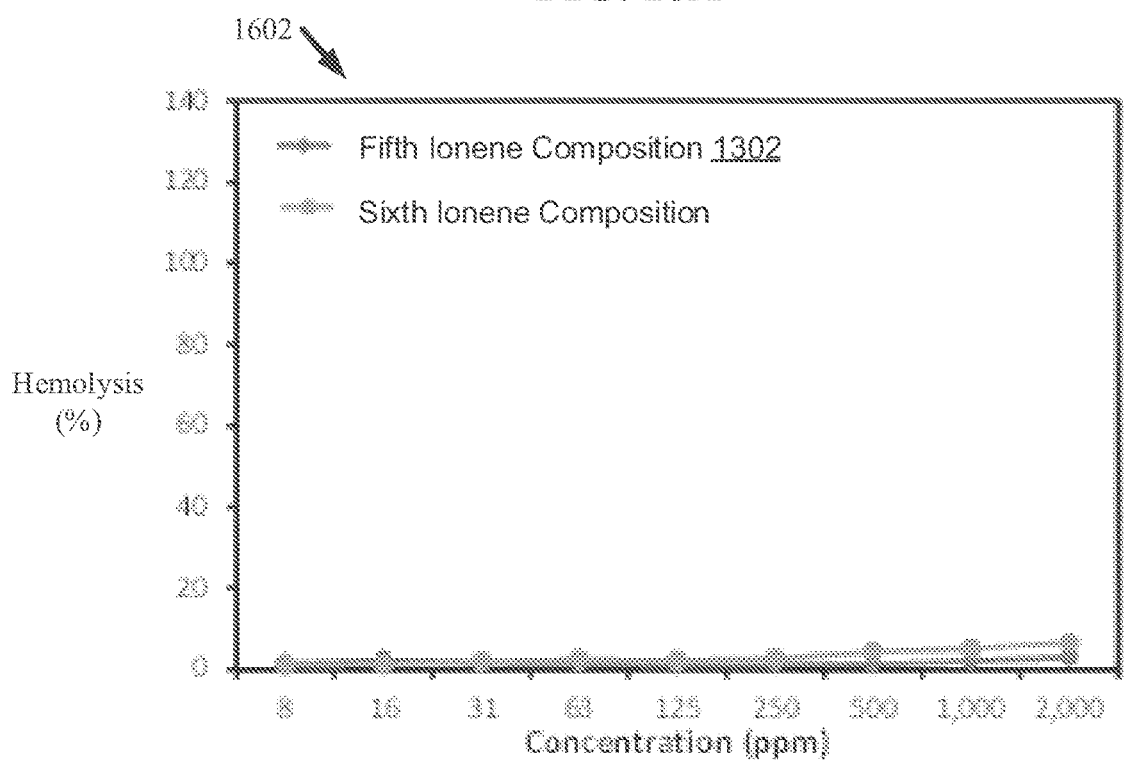
FIG. 16B illustrates a diagram of an example, non-limiting graph that can depict hemolysis activity of various ionene compositions in accordance with one or more of the embodiments described herein.

FIG. 16B illustrates a diagram of an example, non-limiting graph 1602 that can depict the hemolytic activity of various ionene compositions at various concentrations in accordance with the one or more embodiments described herein. Repetitive description of like elements employed in other embodiments described herein is omitted for sake of brevity. For example, graph 1602 can depict the hemolysis activity of the fifth ionene composition 1302, and a sixth ionene composition. The sixth ionene composition can be characterized by chemical formula:

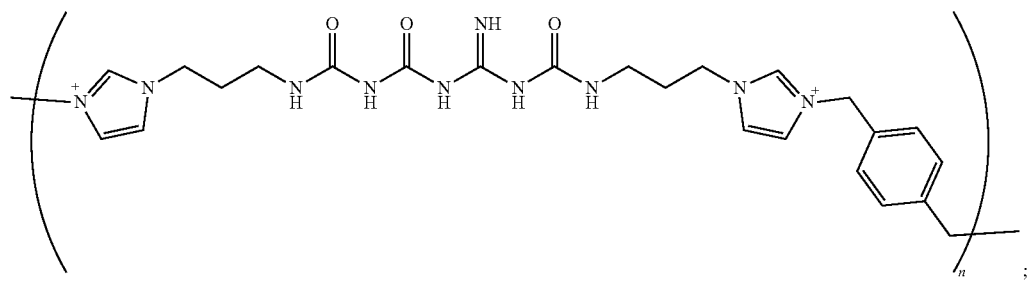

wherein "n" can be an integer greater than or equal to one and less than or equal to one thousand.

FIG. 17 illustrates another flow diagram of an example, non-limiting method 1700 of killing a pathogen, preventing the growth of a pathogen, and/or preventing contamination by a pathogen. Repetitive description of like elements employed in other embodiments described herein is omitted for sake of brevity. Example pathogens include, but are not limited to: Gram-negative bacteria, Gram-positive bacteria, fungi, yeast, a combination thereof, and/or the like.

At 1702, the method 1700 can comprise contacting the pathogen with a chemical compound (e.g., an ionene, a polyionene, a monomer, and/or a polymer). The chemical compound can comprise an ionene unit 100 (e.g., characterized by chemical formula 500, 800, and/or 1100). The ionene unit 100 can comprise a cation 104 (e.g., a nitrogen cation cation) distributed along a degradable molecular backbone 102 that can comprise one or more bis(urea) structures (e.g., derived from 1,3-bis(butoxycarbonyl)guanidine). The ionene unit 100 can have antimicrobial functionality and/or supramolecular assembly functionality.

At 1704, the method 1700 can comprise electrostatically disrupting a membrane of the pathogen (e.g., via lysis process 108) upon contacting the pathogen with the chemical compound (e.g., an ionene unit 100 characterized by chemical formula 500, 800, and/or 1100). Additionally, contacting the pathogen with the chemical compound (e.g., ionene unit 100 characterized by chemical formula 500, 800, and/or 1100) can disrupt the membrane through hydrophobic membrane integration (e.g., via lysis process 108).

The ionene unit 100 that can comprise the chemical compound contacting the pathogen at 1702 can comprise one or more embodiments of the ionene unit 100 and can be characterized by one or more embodiments of chemical formula 500, 800, and/or 1100. For instance, the ionene unit 100 can comprise a molecular backbone 102 that can comprise one or more cations 104 (e.g., represented by "X" in chemical formula 500, 800, and/or 1100), one or more bis(urea)guanidinium structures (e.g., as shown in FIGS. 2, 4-5, 7-8, 10-11, and/or 13), one or more hydrophobic functional groups 106 (e.g., represented by "R" in chemical formula 500, 800, and/or 1100), and/or one or more functional groups to impart additional degradability (e.g., represented by $R_3$ in chemical formula 1100). The one or more cations 104 can be nitrogen cations (e.g., quaternary ammonium cations, imidazolium cations, and/or a combination thereof) and/or phosphorus cations (e.g., quaternary phosphonium cations). Further, one or more of the cations 104 can be bonded to one or more of the hydrophobic functional groups 106. Additionally, the ionene unit 100 can repeat a number of times greater than or equal to 1 and less than or equal to 1000. Therefore, the ionene unit 100 contacting the pathogen at 1702 can comprise any and all the features of various embodiments described herein.

The various structures (e.g., described regarding FIGS. 1-2, 5, 8, and/or 11), compositions (e.g., described regarding FIGS. 4, 7, 10, and/or 13-16B), and/or methods (e.g., described regarding FIGS. 3, 6, 9, 12, and/or 17) described herein can regard various chemical compounds that can be incorporated into a variety of applications. For example, said applications can include cleaning, sanitizing, disinfecting, and/or otherwise treating various articles such as, but not limited to: food packaging, medical devices, floor surfaces, furniture surfaces, wound care instruments (e.g., bandages and/or gauss), building surfaces, plants (e.g., agricultural crops), ground surfaces, farming equipment, beds, sheets, clothes, blankets, shoes, doors, door frames, walls, ceilings, mattresses, light fixtures, facets, switches, sinks, grab rails, remote controls, vanities, computer equipment, carts, trolleys, hampers, bins, a combination thereof, and/or the like. In another example, said applications can include pharmaceuticals, pharmaceutical salts, hygiene products (e.g., soaps and/or shampoos), and/or the like. In a further example, said applications can include agricultural sprays and/or aqueous solutions that can facilitate processing crops for consumption.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

What has been described above include mere examples of systems, compositions, and methods. It is, of course, not possible to describe every conceivable combination of reagents, products, solvents, and/or articles for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A chemical compound comprising:
an ionene unit comprising a cation distributed along a degradable backbone, the degradable backbone comprising a bis(urea)guanidinium structure, wherein the ionene unit has antimicrobial functionality.

2. The chemical compound of claim 1, wherein the cation is selected from the group consisting of a nitrogen cation and a phosphorus cation.

3. The chemical compound of claim 1, wherein the cation is a nitrogen cation selected from the group consisting of a protonated secondary amine cation, a protonated tertiary amine cation, a quaternary ammonium cation and an imidazolium cation.

4. The chemical compound of claim 1, wherein the cation is covalently bonded to a hydrophobic functional group.

5. The chemical compound of claim 4, wherein the ionene unit has a structure characterized by Formula 1:

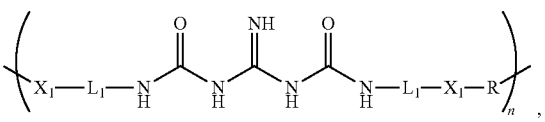

Formula 1 wherein $X_1$ represents the cation, wherein R represents the hydrophobic functional group, wherein n represents an integer greater than or equal to one and less than or equal to one thousand, and wherein $L_1$ represents a linkage group selected from the group consisting of an alkyl group and an aryl group.

6. The chemical compound of claim 5, wherein the cation is a nitrogen cation selected from the group consisting of a protonated secondary amine cation, a protonated tertiary amine cation, a quaternary ammonium cation and an imidazolium cation.

7. The chemical compound of claim 5, wherein the chemical compound further comprises a second ionene unit covalently bonded to the ionene unit, wherein the chemical compound has another structure characterized by Formula 2:

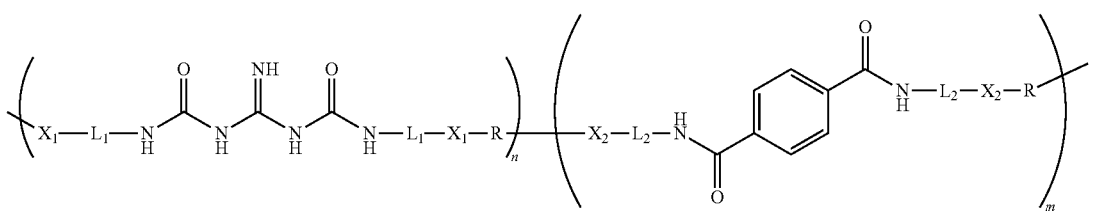

Formula 2 wherein $X_2$ represents a second cation, wherein m represents a second integer greater than or equal to one and less than or equal to one thousand, and wherein $L_2$ represents a second linkage group selected from the group consisting of a second alkyl group and a second aryl group.

8. The chemical compound of claim 1, wherein the chemical compound has a structure selected from the group consisting of:

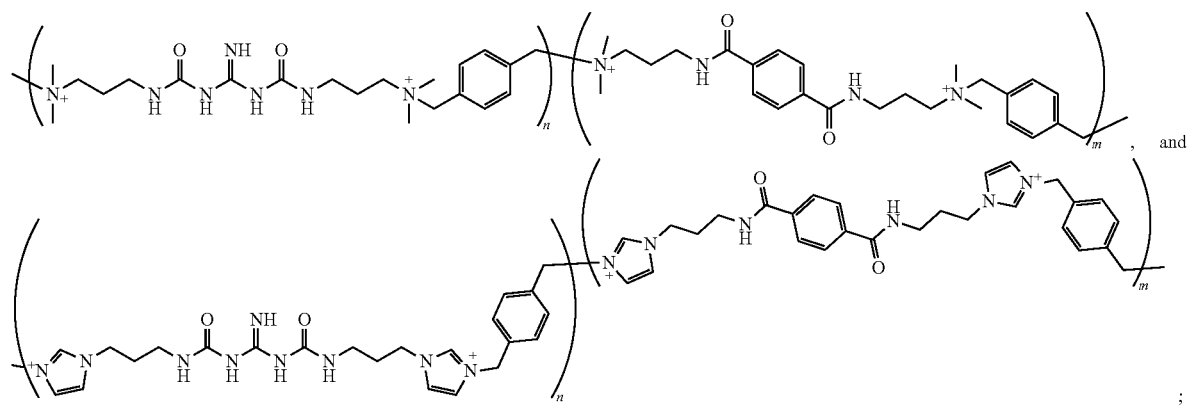

wherein n represents a first integer greater than or equal to one and less than or equal to one thousand; and
wherein m represents a second integer greater than or equal to one and less than or equal to one thousand.

9. The chemical compound of claim 1, wherein the ionene unit has a structure characterized by Formula 1:

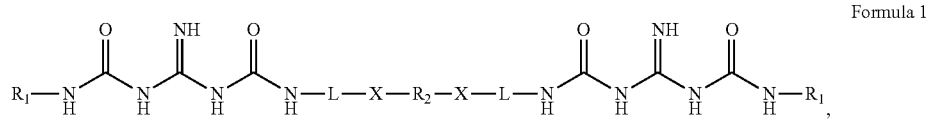

Formula 1 wherein $R_1$ represents an ester group, wherein X represents the cation, wherein $R_2$ represents a hydrophobic functional group, and wherein L represents a linkage group selected from the group consisting of an alkyl group and an aryl group.

10. The chemical compound of claim 1, wherein the chemical compound has a structure characterized by Formula 1:

Formula 1

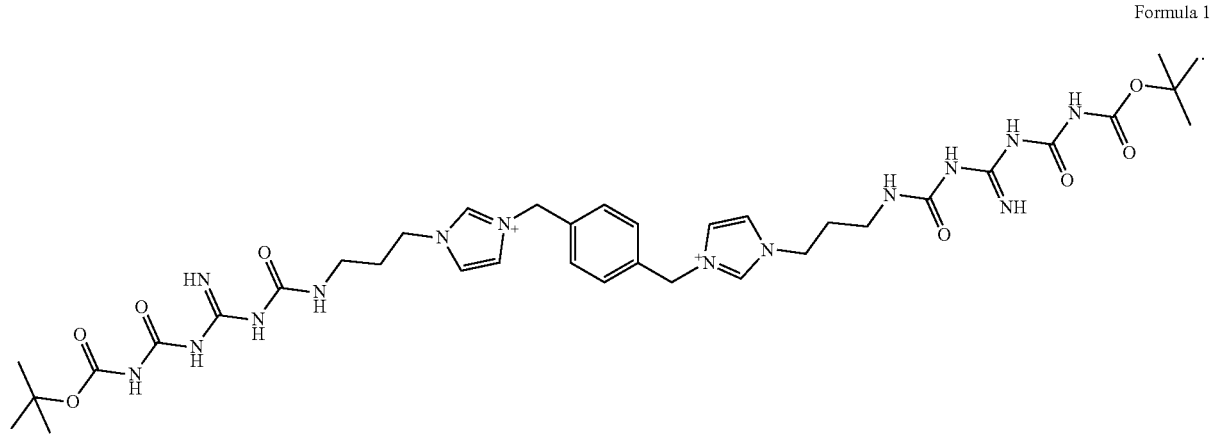 [SMILES: CC(C)(C)OC(=O)NC(=O)NC(=N)NC(=O)NCCCn1cc[n+](Cc2ccc(C[n+]3ccn(CCCNC(=O)NC(=N)NC(=O)NC(=O)OC(C)(C)C)c3)cc2)c1]

* * * * *